(12) United States Patent
Bowersock et al.

(10) Patent No.: US 7,160,544 B2
(45) Date of Patent: Jan. 9, 2007

(54) METHOD OF VACCINATING VERTEBRATES

(75) Inventors: Terry L. Bowersock, Portage, MI (US); Paul Guimond, Kalamazoo, MI (US); Tzu-Chi R. Ju, Thousand Oaks, CA (US); Argaw Kidane, Greensboro, NC (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 180 days.

(21) Appl. No.: 10/705,660

(22) Filed: Nov. 10, 2003

(65) Prior Publication Data

US 2004/0071727 A1 Apr. 15, 2004

Related U.S. Application Data

(62) Division of application No. 09/853,919, filed on May 11, 2001, now Pat. No. 6,656,470.

(51) Int. Cl.
*A61K 9/14* (2006.01)

(52) U.S. Cl. .............. 424/184.1; 424/185.1; 424/277.1

(58) Field of Classification Search ............. 424/184.1, 424/489
See application file for complete search history.

(56) References Cited

U.S. PATENT DOCUMENTS

| | | | |
|---|---|---|---|
| 3,551,556 A | 12/1970 | Kliment et al. | 424/21 |
| 3,880,990 A | 4/1975 | Bauer et al. | 424/19 |
| 4,178,361 A | 12/1979 | Cohen et al. | 424/22 |
| 4,220,152 A | 9/1980 | Dresback | 128/260 |
| 4,352,883 A | 10/1982 | Lim | 435/178 |
| 4,391,909 A | 7/1983 | Lim | 435/178 |
| 4,673,566 A | 6/1987 | Goosen et al. | 424/19 |
| 4,689,293 A | 8/1987 | Goosen et al. | 435/1 |
| 4,780,315 A | 10/1988 | Wu et al. | 424/438 |
| 4,792,452 A * | 12/1988 | Howard et al. | 424/475 |
| 4,798,786 A | 1/1989 | Tice et al. | 435/177 |
| 4,803,168 A | 2/1989 | Jarvis, Jr. | 435/240.22 |
| 4,806,355 A | 2/1989 | Goosen et al. | 424/424 |
| 4,808,404 A | 2/1989 | Bhogal | 424/88 |
| 4,873,090 A | 10/1989 | Clancy | 424/451 |
| 5,019,100 A * | 5/1991 | Hennink et al. | 623/6.56 |
| 5,075,109 A | 12/1991 | Tice et al. | 424/88 |
| 5,352,448 A | 10/1994 | Bowersock et al. | 424/438 |
| 5,674,495 A | 10/1997 | Bowersock et al. | 424/184.1 |
| 6,214,331 B1 | 4/2001 | Vanderhoff et al. | 424/78.17 |
| 6,656,470 B1 * | 12/2003 | Bowersock et al. | 424/184.1 |

FOREIGN PATENT DOCUMENTS

| | | |
|---|---|---|
| EP | 0 188 309 A2 | 7/1986 |
| EP | 0 540 413 A1 | 5/1993 |
| JP | 1-313437 | 12/1989 |
| WO | WO 85/00752 A | 2/1985 |
| WO | WO 95/02416 | 1/1995 |
| WO | WO 98/46211 | 10/1998 |
| WO | WO 01/00233 | 1/2001 |

OTHER PUBLICATIONS

Bowersock et al., "Evaluation of an orally administered vaccine, using hydrogels containing bacterial exotoxins of *Pasteurella hoemolytica*, in cattle", American Journal of Veterinary Research, vol. 55, No. 4, pp. 502-509 (1994).
Bowersock et al., "Oral Administration of Mice with Ovalbumin Encapsulated in Alginate Microspheres". Abstracts of Papers of the American Chemical Society. vol. 208 (1994).
Bowersock et al., "Oral Vaccination of Animals Via Hydrogels", Proceed. Intern. Symp. Control. Rel. Bioact. Mater., vol. 21 (1994).
Bowersock et al., "Uptake of Alginate Microspheres by Peyer's Patches", Proceed Intern. Symp. Control. Rel. Bioact. Mater., vol. 21 (1994).
Offit et al., "Enhancement of Rotavirus Immunogenicity by Microencapsulation", Virology, vol. 203, pp. 134-143 (1994).
Suckow et al., "Stimulation of Immunity to *Pasteurella multocida* in Rabbits by Oral Immunization Using a Microsphere Delivery System", Proceed. Intern. Symp. Control. Rel. Bioact. Mater., vol. 21 (1994).
Jackson, R. "Aliginate Microspheres for Oral Delivery of Vaccines" a Thesis Submitted to the Faculty of Purdue University (1995).

(Continued)

Primary Examiner—Christina Chan
Assistant Examiner—Yunsoo Kim
(74) Attorney, Agent, or Firm—Pharmacia & Upjohn Company; Thomas A. Wootton

(57) ABSTRACT

The invention provides a vaccine composition and a method of preparation including the steps of: forming a water-in-oil emulsion including an alginate in water, an oil, an antigen, and either (a) a cellulose ether and at least one nonionic surfactant or (b) a PEO-PPO-PEO triblock copolymer surfactant and at least one nonionic surfactant; followed by crosslinking the alginate in the emulsion with at least two cations selected from the group consisting of aluminum, barium, calcium, lithium, manganese, strontium, and zinc, to form antigen-containing, crosslinked alginate microparticles; and harvesting the microparticles. Another aspect of the invention is a method of vaccinating a vertebrate species including the step of administering to the species a vaccine composition prepared according to the method of the invention. The compositions of the invention have improved antigen loading, reduced microparticle size, increased hydrophobicity, improved uptake by antigen sampling cells, controlled antigen release characteristics, and improved immunogenicity.

65 Claims, 25 Drawing Sheets

OTHER PUBLICATIONS

Figure 1:
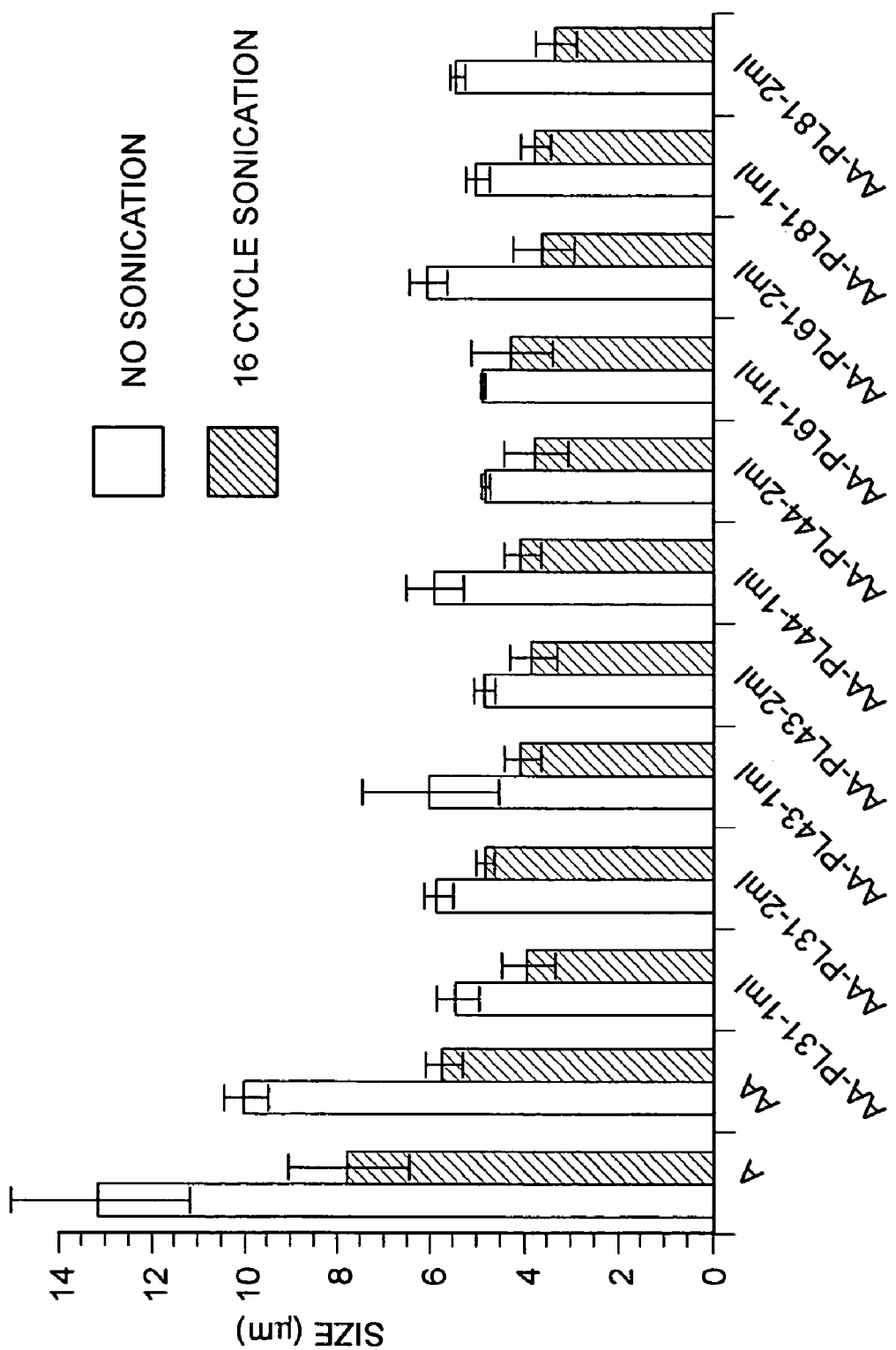

Khoury et al., "Oral Inoculation of Mice with Low Doses of Microencapsulated, Noninfectious Rotavirus Induces Virus-Specific Antibodies in Gut-Associated Lymphoid Tissue", *The Journal of Infectious Diseases*, vol. 172, pp. 870-874 (1995).

Bowersock et al., "Adminstration of Ovalbumin Encapsulated in Alginate Microspheres to Mice", Chapter 6 in "Hydrogels and biodegradable polymers for bioapplications", *American Chemical Society*, pp. 58-66 (1996).

Duncan et al., "Comparative analysis of oral delivery systems for live rotavirsu vaccines", *Journal of Controlled Release*, vol. 41, pp. 237-247 (1996).

HogenEsch et al., "Systemic and pulmonary immune response to intrabronchial administration of ovalbumin in calves", *Veterinary Immunology and Immunopathology*, vol. 51, pp. 293-302 (1996).

Moser et al., "Aqueous-based microencapsulation enhances virus-specific humoral immune responses in mice after parenteral inoculation", *Vaccine*, vol. 14, No. 13, pp. 1235-1238 (1996).

Moser et al., "Effect of microencapsulation on immunogenicity of a bovine herpes virus glycoprotein and inactivated influenza virus in mice", *Vaccine*, vol. 15, No. 16, pp. 1767-1772 (1997).

Periwal et al., "Orally Administered Microencapsulated Reovirus Can Bypass Suckled, Neutralizing Material Antibody That Inhibits Active Immunization of Neonates", *Journal of Virology*, vol. 71, No. 4, pp. 2844-2850 (Apr. 1997).

Bowersock et al., "Induction of pulmonary immunity in cattle by oral administration of ovalbumin in alginate microspheres", *Immunology Letters*, vol. 60, pp. 37-43 (1998).

Cho et al., "Novel mucosal immunization with polysaccharide-protein conjugates entrapped in alginate microspheres", *Journal of Controlled Release*, vol. 53, pp. 215-224 (1998).

Jarvinen, "Mucosal Vaccination of Rabbits Against *Pasteurellosis* Using *Pasteurella multocida* Toxin (PT) and a Potassium Thiocyanate Extract of *P. multocida* (CN) Encapsulated in Sodium Alginate Microspheres" A Thesis Submitted to the Faculty of Purdue University, May 1997, (released from confidentiality on Oct. 19, 1998).

Moser et al., "Relative Importance of Rotavirus-Specific Effector and Memory B Cells in Protection against Challenge", *Journal of Virology*, vol. 72, No. 2, pp. 1108-1114 (1998).

Bowersock et al., "Oral vaccination of animals with antigens encapsulated in alginate microspheres", *Vaccine*, vol. 17, pp. 1804-1811 (1999).

MSDS for Alginic Acid, Sodium Salt by Acros Organics U.S.A. of Fair Lawn, New Jersey (Jun. 4, 1999).

Jarvinen et al., "Intranasal Vaccination of New Zealand White Rabbits Against *Pasteurellosis*, Using Alginate-Encapsulated *Pasteurella multocida* Toxin and Potassium Thiocyanate Extract", *Comparative Medicine*, vol. 50, No. 3, pp. 263-269 (Jun. 2000).

Kidane et al., "The efficacy of oral vaccination of mice with alginate encapsulated outer membrane proteins of *Pasteurella haemolytica* and One-Shot® ", *Vaccine*, vol. 19, pp. 2637-2646 (2001).

Mittal et al., "Immunization with DNA, adenovirus or both in biodegradable alginate microspheres: effect of route of inculation on immune response", *Vaccine*, vol. 19, pp. 253-263 (2001).

Product Bulletin for Structured Foods with the Algin/Calcium Reaction: Kelco corp. (date unknown).

International Search Report (PCT) dated Feb. 14, 2002, mailed Mar. 22, 2002, for PCT/US01/15235.

Chan et al., "Effect of cellulose derivatives on alginate microspheres prepared by emulsification", *J. Microencapsulation*, vol. 14, No. 5, pp. 545-555 (1997).

Lemoine et al., "Preparation and characterization of alginate microspheres containing a model antigen", *International Journal of Pharmaceutics* 176, pp. 9-19 (1998).

C.J. Gray and J. Dowsett, "Retention of Insulin in Alginate Gel Beads" Biotechnology and Bioengineering, vol. 31, pp. 607-612 (1988).

Jackson, R. et al., "*Preparation of 2-5 μm alginate microparticles by emulsification for oral vaccine delivery: Effects of surfactant type, crosslinker, and mixer speed on particle size,*" Pharmaceutical Research (New York), vol. 14, No. 11 Suppl., Nov. 1997, pp. S47-S48, XP008000504, Annual Meeting of the American Association of Pharmaceutical Scientists; Boston, Massachusetts, USA; Nov. 2-6, 1997, ISSN: 0724-8741.

\* cited by examiner

METHOD OF VACCINATING VERTEBRATES

CROSS REFERENCE TO RELATED APPLICATION

This is a divisional of U.S. application Ser. No. 09/853,919, filed May 11, 2001, now U.S. Pat. No. 6,656,470.

BACKGROUND OF THE INVENTION

1. Field of the Invention

The invention relates generally to a composition and method for vaccinating vertebrate species, and to a method of preparing the composition. More specifically, the invention relates to a vaccine composition including an antigen in modified alginate microparticles, a method of making the vaccine composition, and a method of vaccinating using the composition to induce immunity.

2. Brief Description of Related Technology

Historically, immunization has relied upon the induction of humoral immunity by parenteral administration of vaccines. Antibodies induced by parenteral administration, however, do not necessarily reach mucosal surfaces, the sites of entry of most infectious agents. Mucosal immunity, which develops at mucosal surfaces as a result of contact of antigen with mucosal lymphoid tissues, is an important first line of defense against infectious agents.

Induction of immunity at mucosal surfaces requires direct contact of antigen with a mucosal surface. This is not always possible or practical, however, because of handling and delivery problems and because of the toxicity of some antigens to mucosal surfaces. An alternative way to induce protective immunity at mucosal surfaces is by stimulation of the common mucosal immune system (CMIS), a network immunologically linking all mucosal sites to each other. The CMIS consists of lymphoid tissue at mucosal sites that sample antigens to induce an immune response. Microfold cells (M cells) are the specialized cells that sample antigens so that they can be processed by the lymphocytes and macrophages. Major concentrations of mucosal associated lymphoid tissue are found in the upper respiratory tract, the lower respiratory tract, and the gastrointestinal tract.

The gastrointestinal site contains the greatest concentration of lymphocytes in the body, primarily in areas referred to as Peyer's patches. Stimulation of the lymphoid tissue in the gut (gut associated lymphoid tissue, or GALT) by oral vaccines can result in antigen specific lymphocytes that enter the lymph and general circulation. These lymphocytes home to (migrate back to) the lamina propria of the site of their origin where they then produce antibody that coats the mucosal surface. As part of the CMIS, a significant population of these lymphocytes migrate to other mucosal sites. In this manner, oral administration of antigens can be used to induce mucosal response to provide systemic protection from infection and to prevent infection at a variety of mucosal sites in the body.

The oral route of delivery is the most attractive way to deliver antigens, but at the same time very challenging. For proper immunogenicity by oral antigen delivery using microparticles, the microparticles must be taken up by M cells, transferred to lymphoid follicles, and processed by lymphocytes and macrophages underlying these follicles. Uptake of microparticles by the M cells depends heavily on the nature of the microparticles such as size, hydrophobicity, and possibly surface charge.

Oral vaccine carriers are being studied for delivery of vaccines useful in treatment of a variety of human diseases. Often, oral vaccines are developed using animal models. Information gained from oral vaccines developed for one species can be used for more efficient development of vaccines for other species.

Oral administration of vaccines is easy and economical, with little labor required. Oral administration reduces the chance of adverse reactions and eliminates injection site reactions that can damages the carcass or hide of an animal. However, orally administered antigens must be protected from the low pH and enzymes of the stomach until they reach the GALT in the small intestine. Otherwise, antigens can be damaged or altered, resulting in reduced stimulation and a less effective immune response.

Generally, it is known that alginate gel microparticles (or microspheres) can be used as a matrix for oral delivery of vaccine-relevant antigens. See Bowersock et al., U.S. Pat. No. 5,674,495, issued on Oct. 7, 1997. The advantages of this matrix include compatibility with a wide variety of antigens, including fragile antigens, compatibility with live organisms, compatibility with nucleic acids, and provision of an adjuvant effect by the alginate system itself. Although the basic technique is known, there are many variables that can affect the formation of alginate microparticles, their resulting size, their efficiency in loading antigen, their hydrophobicity, their uptake by antigen sampling cells, their antigen-release characteristics, and the overall immunological response generated when using the microparticles.

While it is known that antigen encapsulated in smaller (e.g., diameter less than 10 µm) alginate microparticles have a greater chance of uptake (phagocytosis) by GALT, formation of microparticles with diameters less than 10 µm using traditional methods can compromise antigen loading. Thus, reducing the size of alginate microparticles while maintaining, or increasing, antigen loading can allow for administration of smaller volumes of vaccine, leading to material conservation.

While it is known that phagocytosis of microparticles increases as the hydrophobicity of the microparticles increases and as the charge on the molecule is more positive, traditional vaccines made with alginate-encapsulated antigen are somewhat hydrophilic, which hinders uptake (phagocytosis) by GALT, and alginate naturally carries a negative charge. Traditional antigen-containing alginate microparticles require coating with polymers, including poly-cations such as poly-1-lysine, to give the microparticles a positive charge and to increase their hydrophobicity, to produce any immunological response. Thus, increasing the hydrophobicity and positive surface charge of antigen-containing alginate microparticles would eliminate or reduce the necessity of polymer coatings, increase uptake by GALT, and improve immunological response.

Finally, traditional vaccines using alginate microparticles require multiple administrations over time to produce sustained antigen delivery to the desired target because the timing of immune system stimulation following administration of vaccines made by traditional methods is unpredictable and is not subject to control. For example, alginate microparticles made by Cho et al., *J. Control. Rel.*, 53, p. 215–224 (1998), released 80% of their antigen within 24 hours. Thus, antigen-containing alginate microparticles which have predictable and controllable antigen-release profiles can eliminate or reduce the necessity for multiple vaccine administrations and can provide sustained antigen delivery to the desired target.

Accordingly, it would be desirable to provide methods and compositions for the treatment of diseases in vertebrate species which have improved antigen loading, reduced microparticle size, increased hydrophobicity, improved uptake by antigen sampling cells, controlled antigen release characteristics, and improved immunogenicity.

SUMMARY OF THE INVENTION

Accordingly, the invention provides a vaccine composition and a method of preparation including the steps of: forming a water-in-oil emulsion including an alginate in water, an oil, an antigen, and at least one of (a) a cellulose ether and at least one nonionic surfactant; and (b) a poly (ethylene oxide)-poly(propylene oxide)-poly(ethylene oxide) triblock copolymer surfactant and at least one nonionic surfactant; followed by crosslinking the alginate in the emulsion with at least two cations selected from the group consisting of aluminum, barium, calcium, lithium, manganese, strontium, and zinc, to form antigen-containing, crosslinked alginate microparticles; and harvesting the microparticles.

Another aspect of the invention is a method of vaccinating a vertebrate species including the step of administering to the species a vaccine composition prepared according to the method of the invention.

Another aspect of the invention is a method of provoking an immune response in a vertebrate species including the step of administering to the vertebrate species a vaccine composition prepared according to the method of the invention.

Further aspects and advantages of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to the specific embodiments described herein.

BRIEF DESCRIPTION OF THE DRAWINGS

FIG. 1 is a graph that shows the effect of oly(ethylene oxide)-poly(propylene oxide)-poly(ethylene oxide) (abbreviated PEO-PPO-PEO) copolymer surfactants and methylcellulose on the mean volume particle size of alginate microparticles.

FIG. 2 is a graph that shows the effect of adding different amounts of various PEO-PPO-PEO copolymer surfactants on bovine serum albumin (BSA) loading efficiency.

FIG. 3 is a graph that shows the effect of poly-1-lysine coating on mean volume particle size for three different alginate formulations.

FIG. 4 is a graph that shows the effect of methylcellulose and PEO-PPO-PEO copolymer surfactants on the hydrophobicity of alginate microparticles as measured by phase partitioning.

FIG. 5 is a graph that shows the effect of poly-1-lysine coating on the hydrophobicity of alginate microparticles, as measured by phase partitioning.

FIG. 6 is a graph that shows the effect of METHOCEL A4C methylcellulose and PLURONIC L61 surfactant on the hydrophobicity of alginate microparticles, as measured by a contact angle measurement technique.

FIG. 7 is a graph that shows the effect of various cation solutions and surfactants on antigen loading efficiency.

FIGS. 8–17 are graphs that show antibody titer results of mice injected subcutaneously with microparticles containing ovalbumin made using several different emulsion formulations, and with various control substances.

FIG. 18 is a graph that shows the effect of adding various PEO-PPO-PEO copolymer surfactants and methylcellulose to a base alginate formulation with TWEEN 85 surfactant on the hydrophobicity of alginate microparticles.

FIG. 19 is a graph that shows the effect of poly(propylene glycol) on alginate microparticle hydrophobicity.

FIG. 20 is a graph that shows the effect of poly-1-lysine coating on microparticle size for various microparticle formulations.

FIG. 21 is a graph that depicts mortality results for groups of mice vaccinated with various alginate microparticle formulations and challenged with live bacteria.

FIG. 22 is a graph that shows the effect of various alginate microparticle formulations on the mean volume size of alginate microparticles.

FIG. 23 is a graph that shows the effect of various alginate microparticle formulations on the hydrophobicity of alginate microparticles, as measured by a contact angle measurement technique.

FIG. 24 is a graph that shows cytotoxicity of alginate microparticles made from different alginate-based formulations towards bovine polymorphonuclear neutrophils.

FIG. 25 is a graph that shows cellular uptake of alginate microparticles by macrophages as measured by flow cytometry using fluorescent FITC-labeled microparticles.

DETAILED DESCRIPTION OF THE PREFERRED EMBODIMENTS

The invention is directed to vaccine compositions, methods of preparation thereof, and methods of vaccinating vertebrate species with a vaccine composition of the invention.

One method of preparing a vaccine composition of the invention includes the steps of: (A) forming a water-in-oil emulsion including (a) water, (b) an alginate, (c) an oil, (d) an antigen, and (e) either (i) a cellulose ether and at least one nonionic surfactant or (ii) a PEO-PPO-PEO triblock copolymer surfactant and at least one nonionic surfactant; then (B) crosslinking the alginate in the emulsion with at least two cations selected from the group consisting of aluminum, barium, calcium, lithium, manganese, strontium, and zinc, to form antigen-containing crosslinked alginate microparticles; and (C) harvesting the microparticles.

The water component used in the method of the invention may be any suitable water that does not otherwise interfere with the production of alginate microparticles. Preferably, deionized water is used to eliminate the presence of metal ions found in hard water, which could interfere with the control of alginate crosslinkage. Preferably, sterile water is used to minimize contamination of the alginate microparticles. Most preferably, sterile, distilled, deionized water (SDDW) is used in the method of the invention.

"Alginate" is a general term used to describe derivatives of alginic acid, including mono- and di-valent salts such as calcium, sodium, or potassium salts, or propylene glycol alginate. Alginates are hydrophilic colloids derived from species of seaweed including *Macrocytis, Ascophyllum*, and *Laminaria* and are available, for example, from Acros Organics Co., Fair Lane, N.J. While any monovalent metallic salt of alginate can be used in the methods of the invention, preferably sodium alginate is used. Sodium alginate is a water-soluble linear polymer which has 1,4'-linked β-D-mannuronic acid and α-L-guluronic acid residues arranged as blocks.

Alginate is also available in a range of suitable viscosity grades from suppliers including Monsanto Company (e.g. KELTONE HV sodium alginate; average viscosity of 400 centipoise (cP) for 1% solution) and Acros Organics, Inc., Fair Lane, N.J. (e.g., "medium viscosity" grade sodium alginate; average viscosity of 350 to 550 centipoise for a 1% solution). Those of skill in the art will understand that the difference in viscosity grades of alginate, when the concentration is the same, roughly corresponds to the average molecular weight of the alginate. Alginate used in the method of the invention preferably will have a viscosity of about 200 centipoise to about 3000 centipoise for a 2% (w/v) solution, more preferably about 350 centipoise to about 2000 centipoise for a 1.5% (w/v) solution. If a lower or higher viscosity grade alginate is used, the size of the alginate microparticles tends to increase, and the loading efficiency tends to decrease. Thus, if a lower or higher viscosity grade alginate were to be used, correspondingly more or less alginate (respectively) as a percentage (w/v) should be used in the method of the invention to approximate the desired alginate solution viscosity.

As the viscosity grade of alginate and the amount used are changed, the amount of each surfactant used according to the method of the invention may need to be changed to achieve optimal size, loading, and hydrophobicity of the microparticles. For example, when using a lower concentration of alginate or a lower viscosity grade of alginate, preferably correspondingly more cellulose ether (and/or a higher molecular weight cellulose ether) is used. For a change in alginate concentration or viscosity grade, preferably the PEO/PPO ratio in a PEO-PPO-PEO triblock copolymer will vary.

Any oil can be used to create an emulsion in the method of the invention, for example, corn oil, safflower oil, olive oil, and canola oil. In the method of the invention, typical grocery store canola oil is preferred for yielding microparticles consistent in size, loading efficiency, and particle formation. Optionally, ultrapure oils (including ultrapure canola oil), which do not contain additives such as surfactants and impurities such as oxidants, may be used.

In the method of the invention, oil can be added in a range of ratios about 1:1 to about 5:1, volume of oil to volume of antigen containing alginate solution (v:v), preferably about 3:1 to about 5:1 (v:v), most preferably about 4:1 (v:v).

Water is used to dissolve the alginate. Preferably, the method of the invention will use a solution of alginate in water in a range of about 1.0% to about 1.5% (w/v), preferably about 1.2% (w/v), when using an alginate with viscosity between about 350 centipoise and about 2,000 centipoise. A particularly advantageous method of preparing the water phase in the method of the invention is to start with a stock solution of about 1.5% to about 3% (w/v) stock alginate solution, and to add antigen to arrive at the final alginate-in-water concentration.

In the presence of cations, the alginate carbohydrates crosslink to form a solid hydrogel. In the method of the invention, at least two cations selected from the group consisting of aluminum, barium, calcium, lithium, manganese, strontium, and zinc are used to crosslink the alginate carbohydrates. Use of a combination of two different cations promotes crosslinkage between different moieties in the mannuronic and guluronic acid portions of the alginate, resulting in a higher degree of crosslinkage and smaller pores. Preferably, a combination of zinc cations and calcium cations is used in the method of invention.

The size, loading, hydrophobicity, and adjuvanticity of alginate microparticles, as well as the onset, duration, and magnitude of immunogenic response all depend, to some degree, on the cation or combination of cations used.

Generally, the cations may be provided by any source which does not otherwise interfere with the formation of alginate microparticles. Suitable sources of cations include non-toxic, water-soluble salts with divalent and/or trivalent cations, and other salts such as sulfates lactates, citrates, tartrates, and acetates. Examples include $AlSO_4$, $BaCl_2$, $CaCl_2$, $MnCl_2$, $ZnCl_2$, calcium acetate, zinc acetate, strontium nitrate, and mixtures thereof.

The preferred sources for zinc and calcium cations are zinc chloride ($ZnCl_2$), calcium chloride ($CaCl_2$), zinc acetate, and calcium acetate, most preferably zinc acetate and calcium acetate. The use of zinc cations results in smaller, firmer, more brittle microparticles, whereas the combination of zinc cations with other cations, including, but not limited to, calcium cations, results in microparticles that are less brittle, with improved dispersion.

Suitable cation concentrations will result in increased microparticle loading efficiency, increased microparticle dispersion, and decreased microparticle size. Preferably, the cation source is added in an amount of about 1 wt. % to about 100 wt. %, more preferably about 5 wt. % to about 80 wt. %, most preferably about 56 wt. % based on the dry weight of alginate when using medium viscosity (e.g., about 350 to about 2,000 cP) sodium alginate. For example, 8 ml of a crosslinker solution including about 9.8% (w/v) zinc acetate and about 4.2% (w/v) calcium acetate is preferably used per 8 ml solution of 1.5% (w/v) medium viscosity (e.g., 400 cP) sodium alginate to make one laboratory scale batch of microparticles in the methods of the invention.

Generally, any nonionic surfactant may be used in the methods of the invention. When an emulsion system is created (e.g. a water-in-oil emulsion), the internal phase (e.g., the aqueous phase) is dispersed within the continuous external phase (e.g., the oil phase). Surfactants coat the dispersed droplets, forming a protective layer. Without being bound by any particular theory, it is believed that this protective layer of surfactants minimizes the interactions between dispersed droplets, creating a stable emulsion. Thickness of the protective layer and surface coverage depends on factors including the nature and concentration of the surfactant. Surfactant molecules are preferentially located at the surface of a microparticle or a dispersed system due to their amphiphilic nature. Depending on the nature of the surfactant molecule, the surface property of a dispersed microparticle can be modified by the surfactant.

A surfactant (or surfactant system including more than one surfactant) can be described by its hydrophile/lipophile balance (HLB) value. HLB values are experimentally determined and assigned on an arbitrary scale from one to forty. If the HLB value is low, there are fewer hydrophilic groups on the surfactant, and it is more lipophilic (oil soluble) than hydrophilic (water soluble). If the HLB value is high, there are more hydrophilic groups on the surfactant and it is more hydrophilic than lipophilic.

The type of surfactant (and surfactant system), HLB, and individual component surfactant(s) can all affect the size, loading, hydrophobicity, and adjuvanticity of alginate microparticles produced by the methods of the invention, as well as the onset, duration, and magnitude of immunogenic response of a resulting vaccine composition made with the microparticles. In the methods of the invention, preferred surfactants (and surfactant systems) have an HLB from about 1 to about 15, more preferably about 7 to about 9, most preferably about 8.3. For oral delivery of microparticles, surfactants that have been approved for use in pharmaceuticals and food preparations are preferred. Examples of suitable approved products are those "Generally Recognized As Safe" (GRAS) by the U.S. Food and Drug Administration (FDA), and those listed in the Food Chemicals Codex, the International Codex Alimentarius, the United States Pharmacopoeia (USP), the European Pharmacopoeia (EP), the Japanese Pharmacopoeia (JP) and British Pharmacopoeia (BP).

Preferably, a nonionic surfactant is selected from the group consisting of polyoxyethylene surfactants, anhydrosorbitol ester surfactants, ethoxylated anhydrosorbitol ester surfactants, and mixtures thereof.

Polyoxyethylene surfactants, also called polyoxyethylene-solubilized nonionics (or ethoxylates) derive their solubility characteristics from recurring ether linkages in a polyoxyethylene chain, —O—$CH_2CH_2$—O—$CH_2CH_2$—O—$CH_2CH_2$—O—, wherein a single oxyethylene group, —$OCH_2CH_2$—contributes slightly more to hydrophilicity than a single methylene, $CH_2$, contributes to hydrophobicity. Most preferably, a polyoxyethylene surfactant used in the method of the invention is an alcohol ethoxylate. Alcohol ethoxylates are sold under the trade names BRIJ, by ICI Americas, Incorporated; ALFONIC, by Condea Vista Corporation; RHODASURF, by Rhone Poulenc, Incorporated; NEODOL, by Shell Chemical Company; and PLURAFAC, by BASF Corporation. Polyoxyethylene(2) olyl ether (also called oleth-2), sold under the name BRIJ 93 by ICI Americas, Inc., is most preferred.

Anhydrosorbitol ester surfactants include fatty acid esters of anhydrosorbitol, particularly the mono-, di-, and triesters of anhydrosorbitols and fatty acids. Anhydrosorbitol ester surfactants are sold under the trade names SPAN and ARLACEL, by ICI Americas, Inc.; ARMOTAN, by Akzo Chemical Company; EMSORB, by Henkel/Emery Corporation; GLYCOMUL, by Lonza, Incorporated; and HODAG, by Calgene Chemical Incorporated. Suitable anhydrosorbitol ester surfactants include sorbitan monolaurate (e.g., SPAN 20 and ARLACEL 20), sorbitan monostearate (e.g., SPAN 60), sorbitan monooleate (e.g., SPAN 80 and ARLACEL 80), sorbitan trioleate (e.g., SPAN 85), sorbitan sesquioleate (e.g., ARLACEL C and ARLACEL 83), and glycerol monooleate (e.g., ARLACEL 186). Sorbitan trioleate (SPAN 85) and sorbitan sesquioleate (ARLACEL 83) are most preferred.

Preferred nonionic surfactant compositions useful in the methods of the invention also include ethoxylated anhydrosorbitol esters, which are also polyoxyethylene derivatives of sorbitan fatty acid esters. Ethoxylated anhydrosorbitol esters are typically more hydrophilic surfactants. Ethoxylated anhydrosorbitol ester surfactants are sold under the trade names TWEEN, by ICI Americas, Inc., ARMOTAN, by Akzo Chemical Co., EMSORB, by Henkel/Emery Corp., GLYCOSPERSE, by Lonza, Inc., and HODAG, by Calgene Chemical Inc. Suitable ethoxylated anhydrosorbitol ester surfactants include polyoxyethylene(20) sorbitan monolaurate, monopalmitate, monostearate, monooleate, and trioleate (e.g., TWEEN 20, 40, 60, 80, and 85; also known as polysorbate 20, 60, 80, and 85). Polyoxyethylene (20) sorbitan trioleate (TWEEN 85) is most preferred.

Polyoxyalkylene derivatives of propylene glycol include triblock copolymers of the formula poly(ethylene oxide)-poly(propylene oxide)-poly(ethylene oxide) ("PEO-PPO-PEO copolymers"). The PEO chain is very hydrophilic, whereas the PPO chain is hydrophobic, resulting in the compounds' surface active behavior. PEO is a flexible chain that, when attached to a microparticle surface, minimizes aggregation by creating a steric barrier. Triblock copolymers such as these that differ in their PEO and/or PPO chain length (i.e., number of ethylene oxide (EO) residues and propylene oxide (PO) residues) are available, for example, under the trade name PLURONIC, sold by BASF Corp.

Without being bound by any particular theory, the PPO chain, part of the PLURONIC surfactant molecule that is hydrophobic, might play a role in improving microparticle hydrophobicity. PLURONIC surfactants tested with 16 PO residues (L31) and 39 PO residues (L81) failed to improve microparticle hydrophobicity, whereas those with PO residues in the range of about 21 to about 30 greatly improved hydrophobicity.

The interaction of the hydrophilic and/or hydrophobic blocks of the PLURONIC surfactant molecules with the aqueous and/or oil phases of the emulsion system may be important in determining the effectiveness of the surfactants in improving hydrophobicity. In the emulsion system, the aqueous alginate droplets are dispersed within a continuous oil phase. A PO residue value that is too high may make the PEO-PPO-PEO copolymer surfactant too hydrophobic, so that it remains in the continuous oil phase. Also, the orientation of this surfactant molecule at the oil/water interface depends on the combined effects of PPO and PEO chain length. The hydrophobic PPO chain of the surfactant molecule tends to orient itself towards the oil phase, whereas the hydrophilic PEO chain interacts favorably with the alginate surface.

Suitable PEO-PPO-PEO copolymers sold as PLURONIC surfactants include those designated L31, L43, L44, L61, and L81 by BASF Corp. Table 1 below gives pertinent data on these PLURONIC surfactants.

TABLE 1

| BASF PLURONIC surfactant designation | Average Mol. Wt. | Viscosity (Brookfield) cP | No. Ethylene Oxide Residues | No. Propylene Oxide Residues | HLB |
|---|---|---|---|---|---|
| L31 | 1,100 | 175 | 2 | 16 | 5 |
| L43 | 1,850 | 310 | 7 | 21 | 12 |
| L44 | 2,200 | 440 | 11 | 21 | 16 |
| L61 | 2,000 | 325 | 3 | 30 | 3 |
| L81 | 2,750 | 475 | 6 | 39 | 2 |

Preferably, a PEO-PPO-PEO copolymer used in the method of the invention has from about 15 to about 70 PO residues, most preferably about 30 PO residues. For example, a preferred PEO-PPO-PEO copolymer useful in the invention having the formula $(EO)_3(PO)_{30}(EO)_3$ is sold under the trade name PLURONIC L61 by BASF Corporation.

In one form of the method of the invention, individual surfactant compositions are blended to prepare a surfactant composition that provides an optimum balance of the desired properties. In a preferred method of the invention, a blend of polyoxyethylene sorbitan trioleate (HLB=11) and PLURONIC L61 surfactant (HLB=3) is used as a surfactant composition.

The amounts of surfactants and surfactant blends useful in the method of the invention are those which result in the best loading of antigen, smallest microparticle size (and, hence, greatest yield of microparticles), greatest degree of hydrophobicity of microparticles and, ultimately, best microparticle uptake by antigen sampling cells and the overall immunological response generated. Optionally, a surfactant blend can be formulated to provide microparticles with controlled antigen-release profiles.

In a preferred method of the invention, polyoxyethylene sorbitan trioleate is used in the range of about 8.3 ml/gram of alginate to about 50 ml/gram of alginate with the copolymer $(EO)_3(PO)_{30}(EO)_3$ in the range of about 8.8 ml/gram alginate to about 24.6 ml/gram alginate. Most preferably, polyoxyethylene sorbitan trioleate is used at about 33.3 ml/gram alginate with the copolymer $(EO)_3(PO)_{30}(EO)_3$ at about 16.7 ml/gram alginate.

The methods and compounds of the invention are not limited with respect to the type of antigen that can be used. Antigen can be mixed with alginate without the need for heat or organic solvents that can otherwise alter and damage antigens. Therefore, alginate can be used to encapsulate a wide variety of antigens, including live viruses and bacteria, labile proteins, and nucleic acids. Preferably, the antigen is selected from the group consisting of live virus, live bacteria, killed virus, killed bacteria, nucleic acids, subunit antigens of infectious agents, and mixtures thereof. Antigens that have been encapsulated by the methods of the invention include live respiratory syncitial virus; live and killed influenza virus; feline calicivirus empty capsids; live *Pseudomonas aeuroginosa*; killed *Pasteurella multocida*, and haemolytica; *E. coli*; bovine, canine, human, equine, and porcine serum albumin and ovalbumin; exotoxin and outer membrane proteins of *P. multocida*, and haemolytica; subunit antigens of *H. pylori*; cytochrome C, and plasmid DNA.

A wide variety of suitable antigen concentrations are useful in the method of the invention. Amount of antigen addition will vary based on factors including the antigen used, the end result desired, and the dosing regimen used. Preferably, antigen is dissolved in a buffer or SDDW to a desired concentration (e.g., about 5 mg/ml to about 50 mg/ml for albumin products), and the stock solution is added to the alginate solution. In a preferred method of the invention, the final concentration of antigen is about 0.5 to about 2.0 mg/ml, more preferably about 1 mg/ml in a 1:1 (w:w) suspension of microparticles in water. Optionally, dehydrated antigen or concentrated soluble antigen can be added directly to the alginate before hydration to increase the concentration of antigen in the alginate in solution, and in the resulting alginate microparticles.

In another form of the method of the invention, a modified cellulose, preferably a cellulose ether, is included in the water-in-oil emulsion either in place of or in addition to the PEO-PPO-PEO copolymer. Microparticles made with cellulose ethers tend to be smaller and more spherical, exhibit better loading efficiency, and have increased hydrophobicity compared to alginate microparticles made only with a single surfactant composition (e.g., polyoxyethylene(20) sorbitan trioleate). Depending on the type of cellulose ethers used, the microparticles may also exhibit prolonged drug release profiles, especially when higher viscosity cellulose ethers are used. Nonionic cellulose ethers are preferred; water-soluble cellulose ethers are also preferred.

Preferably, the cellulose ether is selected from the group consisting of ethylcellulose, methylcellulose, hydroxyethylcellulose, hydroxymethylcellulose, hydroxypropylcellulose, hydroxypropyl methylcellulose, and mixtures thereof Particularly preferred are methylcellulose and hydroxypropyl methylcellulose.

Methylcellulose and hydroxypropyl methylcellulose are water-soluble polymers derived from cellulose, the most abundant polymer in nature. These cellulose derivatives are used in stabilizing emulsions and suspensions by producing a protective colloid around the dispersed droplet or particle. In addition, they can function as surface active agents to aid emulsification and minimize aggregation of the microparticles.

Methylcellulose (sold as the METHOCEL A family of cellulose ethers by the Dow Chemical Company) has a polymer backbone of cellulose, which contains a basic repeating structure of anhydroglucose, with methyl substitution on the anhydroglucose units. Hydroxypropyl methylcellulose products (e.g. METHOCEL E, F, J, and K families of cellulose ethers sold by Dow Chemical), have methyl substitution and hydroxypropyl substitution on the anhydroglucose units. Methylcellulose and hydroxypropyl methylcellulose are available with varying degrees of viscosity, varying degrees of methyl and hydroxypropyl substitution, and with different surface treatments. For example, a particularly preferred methylcellulose, METHOCEL A4C, is a premium food-grade product that has a methoxyl degree of substitution of 1.8, and a viscosity of 400 mPa·s (millipascal-seconds; centipoise). Other preferred coblock cellulose polymers include those sold as METHOCEL K3 and METHOCEL F50 by the Dow Chemical Company.

A cellulose ether (e.g., methylcellulose) is preferably used in a range of ratios about 1:1 to about 1:5, weight of cellulose ether to weight of alginate. Most preferably the ratio is about 1:2 (w:w).

The step of forming a water-in-oil emulsion in the methods of the invention can be performed by any suitable method. Preferably, the emulsion is formed using a high pressure homogenizer, such as the EMULSIFLEX model C5 homogenizer system marketed by Avestin Inc. When the emulsion is formed using a high pressure homogenizer, the oil and water mixture is preferably subjected to two cycles of homogenization at a pressure of about 20,000 PSI. In another preferred form of the invention, the emulsion is formed using a high speed mixer at a speed of least about 500 RPM, preferably at least about 3,000 RPM, most preferably at least about 5,000 RPM.

The cations are preferably added to the emulsion in dropwise fashion, while stirring the emulsion at a speed of at least about 1,000 RPM, preferably about 3,000 to about 6,000 RPM, most preferably about 5,000 to about 6,000 RPM. In this manner, the production of very small (e.g., less than about 10 μm) microparticles is facilitated.

The microparticles may be harvested by any suitable method, including, but not limited to centrifugation, filtration, gravity precipitation, and gradient centrifugation. Preferably, the microparticles are harvested by centrifugation, washed twice in SDDW, once in 10% ethyl alcohol, followed by another wash in SDDW, and suspended in an equal amount, by weight, of SDDW until used.

The emulsion used to produce vaccine compositions via the methods of the invention optionally includes poly (polypropylene glycol) (PPG; also called poly (propylene oxide)). Use of poly(propylene glycol) increases the hydrophobicity of alginate microparticles, especially when a cellulose ether is also used, without a significant effect on microparticle size or loading efficiency.

Optionally, the harvested microparticles can be coated with a polymer. Coating the microparticles with a polymer can improve loading efficiency of the microparticles, increase the strength and hydrophobicity of the microparticles, and decrease the release rate of antigen from the microparticles. Preferably, the polymer is a poly-cation, a cationic (positively charged) polymer. Preferred poly-cations include, but are not limited to, poly-1-lysine, polyhistidine, polyarginine, polyethyleneimine, and mixtures thereof Poly-1-lysine is most preferred.

The microparticles may be coated with polymer by any suitable method, or by suspending the microparticles in a vortex created in a conical tube and slowly adding a solution containing the polymer while maintaining the vortex, allowing the microparticles and polymer to mix for 30 minutes, and then washing with SDDW to remove unreacted polymer.

Optionally, the harvested microparticles can be coated with a mucosal adjuvant/adhesant. Mucosal adjuvants/adhesants include molecules for which there are corresponding receptors on M-cells, epithelial cells, or both. Preferred mucosal adjuvants/adhesants include, but are not limited to, lectins, cholera toxin, B subunit toxin of cholera toxin, recombinant derived subunits of B subunit toxin of cholera toxin, pertussis toxin, heat labile toxin of *E. coli*, exotoxin A of *P. aeruginosa*, and mixtures thereof. Mucosal adjuvants/adhesants may be used alone or in combination with a polymer coating such as poly-1-lysine. For example, some lectins bind directly to alginate, and can be used without a polymer coating. When used with a polymer coating, the mucosal adjuvant/adhesant preferably is coated last.

The microparticles may be coated with a mucosal adjuvant/adhesant by any suitable method. Preferably, the microparticles are coated by adding the mucosal adjuvant/adhesant to a microparticle suspension, vortexing to mix the solution, and washing with SDDW.

The microparticles may be administered by any suitable method, including subcutaneously, orally, intranasally, vaginally, rectally, and by intramammary administration. Oral administration is preferred.

EXAMPLES

The following examples are provided to illustrate the invention but are not intended to limit the scope of the invention.

Example 1

Effect of Methylcellulose and PEO-PPO-PEO Copolymer Surfactants on Microparticle Size, Loading Efficiency, and Hydrophobicity Alginate microparticles were made by an emulsion crosslinking technique. A 1.5% (w/v, i.e., g/100 ml) solution (8 ml/batch) of medium viscosity grade sodium alginate (400 cP viscosity; Acros Organics) was made with SDDW. Methylcellulose (METHOCEL A4C; Dow Chemicals, Midland, Mich.), when used, was first added to the alginate solution to a final concentration of 0.5% (w/v). TWEEN 85 surfactant (4 ml/batch, added to all samples; Sigma-Aldrich, Inc., St. Louis, Mo.) and PLURONIC surfactants (2 ml/batch, when used; BASF Corp., Mount Olive, N.J.) were added to the oil phase, which comprised canola oil (40 ml/batch; Meijer, Inc., Kalamazoo, Mich.).

To prepare alginate microparticles containing antigen, a 2 ml solution of bovine serum albumin (BSA, Sigma-Aldrich, Inc.) was first mixed with the 1.5% (w/v) alginate (plus methylcellulose, when used) solution to a final concentration of 1 mg/ml. The water phase was subsequently added to the oil phase in a volume ratio of 1:4. An emulsion was created by homogenizing the mixture using a homogenizer (EMULSIFLEX model C-5, Avestin Inc., Ottawa, Canada). The mixture was subjected to two cycles of homogenization at a pressure of 20,000 PSI for effective emulsification of the alginate droplets in the continuous oil phase. The alginate droplets were stabilized by cross-linking with an 8 ml mixture of calcium acetate and zinc acetate (4 ml of 4.2% (w/v) calcium acetate, EM Science, Gibbstown, N.J. and 4 ml of 9.8% (w/v) zinc acetate, Sigma-Aldrich, Inc.). The crosslinking solution was added dropwise to the emulsion system at a flow rate of 20 ml/min while stirring the emulsion at a speed of 5,000 RPM. The stirring speed was subsequently raised to 6,000 RPM and maintained at this speed for two minutes. The microparticles were harvested by centrifuging at a speed of 3,500 RPM at 5° C. for 20 minutes. Microparticles were washed three times with SDDW and once with 10% ethanol, then suspended in SDDW at 1:1 (w/w) and stored at 4° C. until evaluated for microparticle size, BSA loading efficiency, and surface hydrophobicity.

Alginate microparticles were coated with poly-1-lysine (PLL, molecular weight (MW) 20,000 Daltons; Sigma-Aldrich, Inc.) to improve stability and enhance hydrophobicity. A 0.2% (w/v) fresh solution of PLL in SDDW was made. A volume of the PLL solution equal to the volume of the microparticle suspension was added to a sonicated (Branson Sonifier 450, Danbury, Conn.; 40% of duty cycle of 60 Hz for 15 seconds per sample) alginate microparticle suspension, and the tube was vortexed for two minutes. It was then shaken on a mechanical shaker (S/P ROTATOR V, Baxter Diagnostics Inc., Deerfield, Ill.) for 10 minutes at 180 RPM. The tube was centrifuged at 3,000 RPM for ten minutes at room temperature to harvest the PLL-coated microparticles. The pellet was washed with SDDW once and re-suspended in SDDW at 1:1 (w/w).

The binding of poly-1-lysine to the alginate microparticles was verified using a microtiter plate fluorometer (Cambridge Technology, Inc., Watertown, Mass.) with fluorescein isothiocyanate (FITC)-labeled poly-1-lysine (PLL-FITC, Sigma-Aldrich, Inc.), and was also observed by fluorescence microscopy.

Particle size was measured using an ACUSIZER 770 optical particle sizer equipped with an autodiluter system (Particle Sizing Systems, Inc., Santa Barbara, Calif.). The ACUSIZER 770 optical particle sizer directly measures the number and sizes of particles greater than or equal to 1 μm by a single particle optical sensing method based on light obstruction. It also determines a volume-weight mean size. A 10-fold dilution (by volume) of the original microparticle suspension was made in SDDW. Microparticle size was determined before and after 16 cycles of sonication.

Loading efficiency was determined using the Pierce micro bicinchoninic acid (BCA) protein assay reagent kit (Pierce, Inc., Rockford, Ill.). Alginate microparticles were lysed by mixing them with an equal volume of 10× phosphate-buffered saline without calcium and magnesium in a test tube. The test tube was placed on a rocking platform (Orbitron Rotator I, Boekel Indus., Inc., Feasterville, Pa.) and rocked overnight. The mixture was centrifuged to separate the alginate fragments from the BSA solution. The supernatant was analyzed for BSA using BCA as the detection reagent.

Microparticle hydrophobicity was evaluated using both a phase partitioning and a contact angle measuring technique. In the phase partitioning technique, microparticle hydrophobicity was evaluated by partitioning a dilute suspension of microparticles between n-octane and water in a modification of a method used to evaluate hydrophobicity of bacteria. See Magnusson et al. "Partitioning of bacteria, virus and phage" in *Partitioning in aqueous two phase systems*, H. Walter, D. Brooks, and D. Fisher, eds., Academic Press, Inc., NY p. 415 (1985). An aqueous alginate microparticle suspension with an optical density reading of 0.5 at 400 nm was used as the aqueous phase. Optical density was read at 400 nm on the aqueous suspension using a UV/visible spectrophotometer (DU Spectrophotometer, Beckman Co., Fullerton, Calif.). Octane (n-octane, 0.2 ml) was then added to the test tube containing the alginate microparticle suspension (1.2 ml) and incubated at room temperature for ten minutes. The test tube containing the two phases was vortexed for two minutes and let stand for fifteen minutes for complete separation of the aqueous and organic phases. Optical density readings were taken on the aqueous phase at 400 nm. The hydrophilicity index (HI) was calculated as the ratio between the initial and final optical density readings.

The phase partitioning technique was validated using latex beads with known surface properties. Polystyrene and poly(styrene-divinyl benzene) microbeads (2.9 µm average diameter, Sigma-Aldrich, Inc.) were used. Washed polystyrene microbeads were also examined for hydrophobicity because the polystyrene suspension obtained contained surface active agents to stabilize the suspension.

For contact angle measurement, clean glass slides were first exposed to a 0.2% (w/v) PLL solution for 30 minutes. The slides were then blotted dry and then exposed to alginate microparticles suspended in SDDW (1:1, w:w). Care was taken to spread the microparticle suspension uniformly over the glass surface. Microparticle-coated glass slides were dried at room temperature overnight. Examination by light microscopy revealed few cracks or defects, due to the gentle drying process. Water contact angle of the dried film of microparticles was measured using a contact angle goniometer (Rame-Hart Inc., Mountain Lakes, N.J.) equipped with a sessile dropper. Five readings were taken for each sample and averaged.

FIG. 1 shows the effect of PLURONIC surfactants and methylcellulose (METHOCEL A4C) on the mean volume particle size of alginate microparticles. Formulation A was the base alginate formulation (made with TWEEN 85 surfactant), whereas AA indicates a formulation that additionally includes methylcellulose, and PL31–PL81 indicate formulations that include TWEEN 85 with PLURONICS L31–L81 surfactants. Results are reported as mean values of three readings, with bars for standard deviations. Alginate microparticles made using TWEEN 85 surfactant alone resulted in microparticles having a mean volume particle size of 13.15 µm and 7.81 µm pre- and post-sonication, respectively. The additional use of methylcellulose in the method of formulation reduced mean volume particle size to 10 µm before sonication, and after 16 cycles of sonication the mean volume particle size was reduced to 5.8 µm. In both methods, sonication resulted in an approximately 50% reduction in mean volume particle size of the microparticles. With the use of PLURONIC surfactants, the effect of sonication on microparticle size was found to be less significant. Each PLURONIC surfactant reduced mean volume particle size to about 6 µm or less before sonication, and about 4 µm or less after 16 cycles of sonication. Increasing the concentration of each PLURONIC surfactant in the formulation from one ml per ten ml alginate solution to two ml per ten ml alginate solution did not affect microparticle size for PL31, PL61, and PL81. However, for PL43 and PL44, a concentration-dependent decrease in the mean volume particle size was observed.

Figure 2:
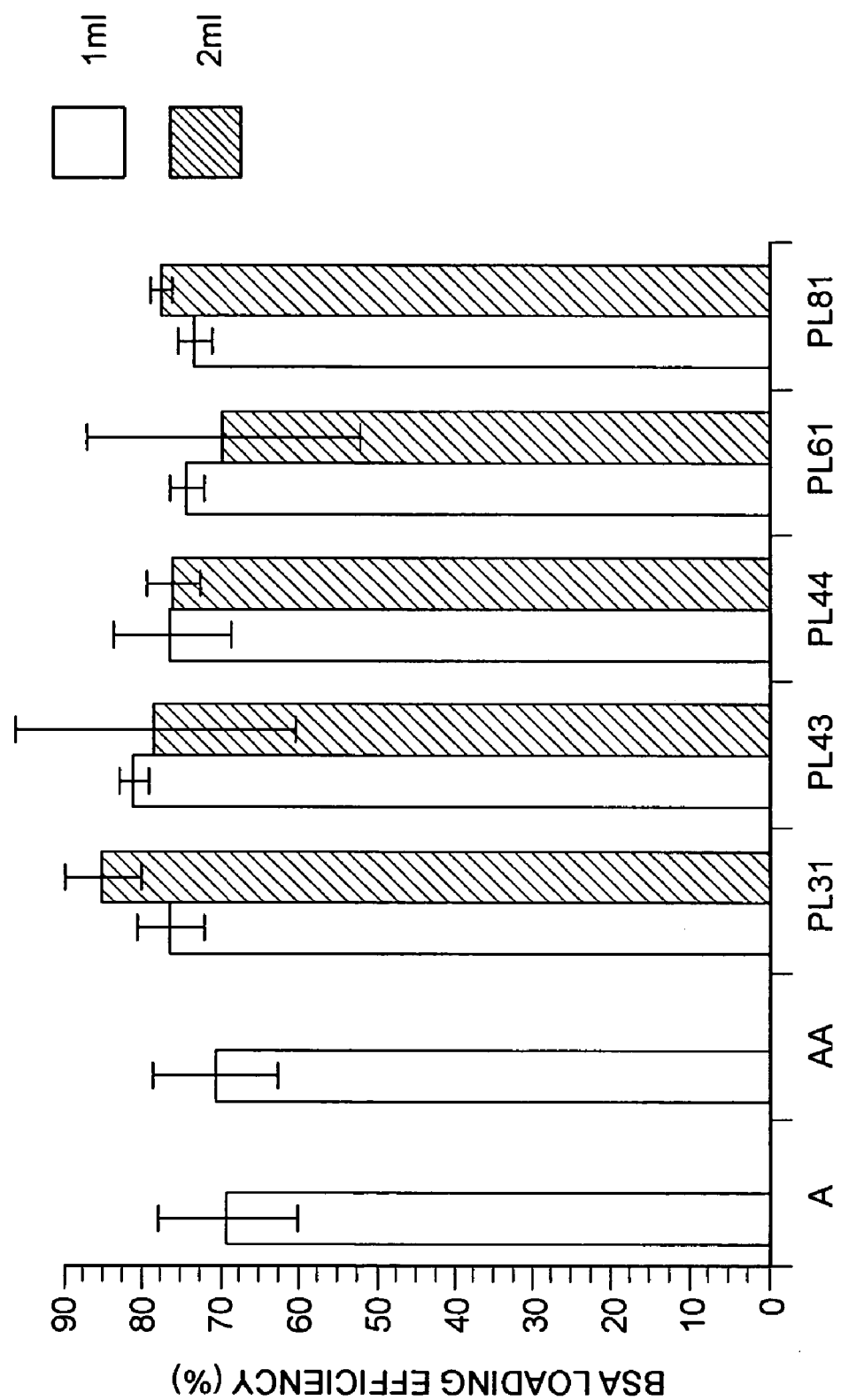

FIG. 2 shows the effect of using different amounts of various PLURONIC surfactants in a microparticle formulation on BSA loading efficiency. Samples are labeled as in FIG. 1, and results are reported as mean values of three samples, with bars for standard deviations. Percent loading efficiency was calculated by comparing the amount of BSA in the microparticles to that which assumes that all BSA added in the formulation was incorporated into the microparticles. The addition of methylcellulose to the base formulation resulted in a slight increase in loading efficiency, and addition of various PLURONIC surfactants to the base formulation resulted in even greater increases in loading efficiency.

Figure 3:
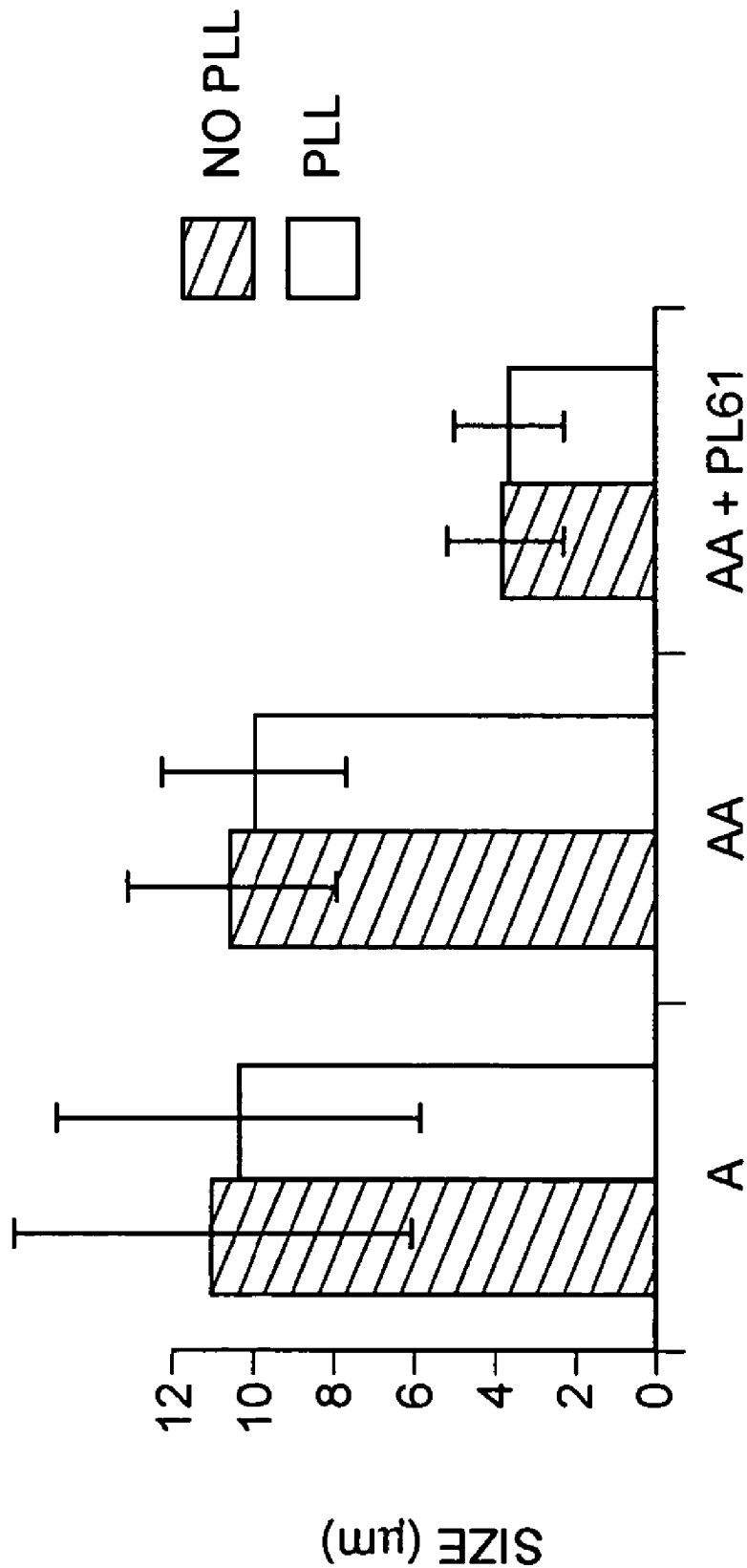

FIG. 3 shows the effect of PLL coating on mean volume particle size for three different alginate formulations. Samples are labeled as in FIG. 1, and results are reported as mean values of three samples, with bars for standard deviations. In all cases, PLL coating did not significantly affect the mean volume size of the microparticles, which shows that PLL coating does not cause aggregation of the microparticles.

Figure 4:
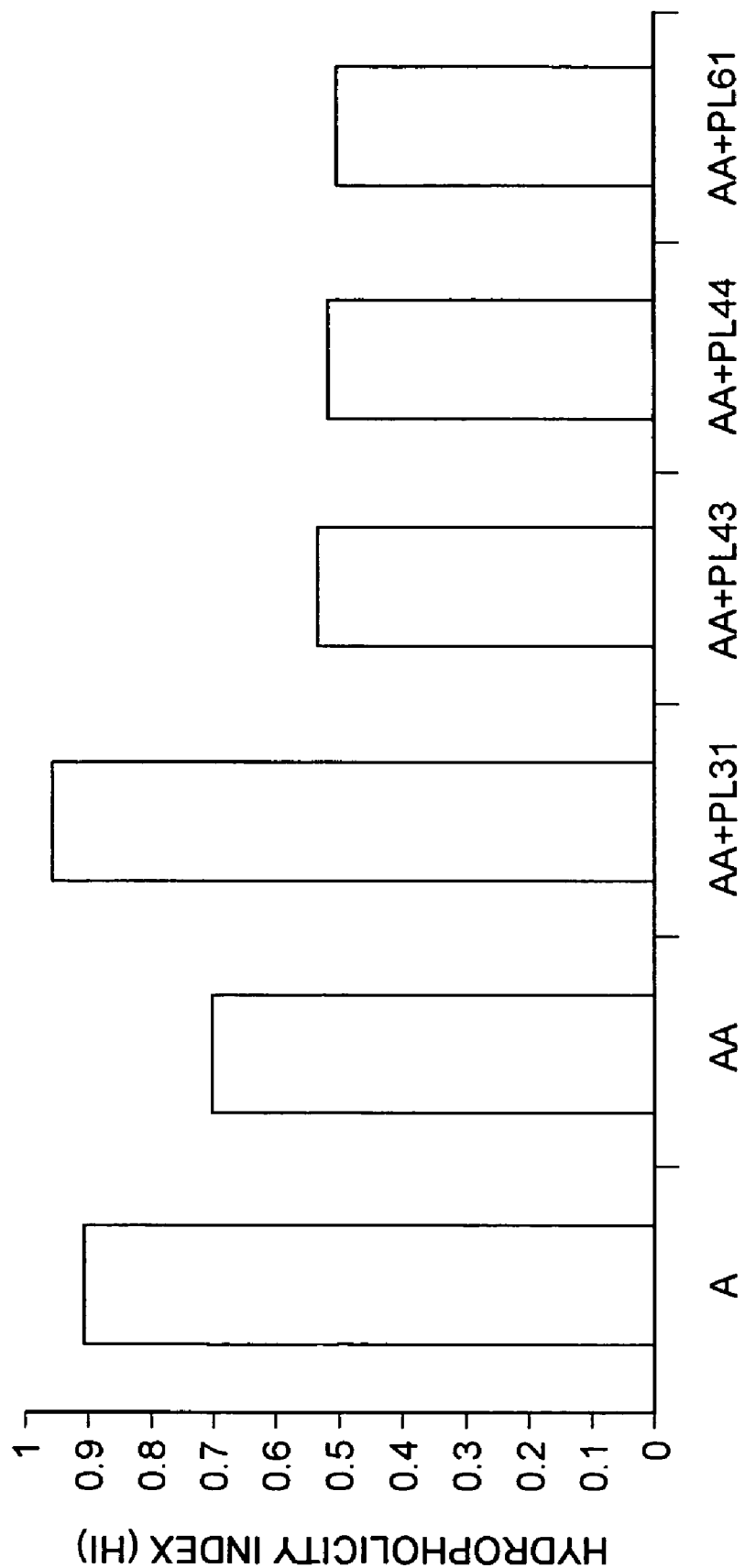

FIG. 4 shows the effect of methylcellulose and PLURONIC surfactants on the hydrophobicity of alginate microparticles as measured by phase partitioning. Samples are labeled as in FIG. 1; results represent one sample per formulation. The addition of methylcellulose to the base alginate formulation reduced the HI values (increased hydrophobicity) of the microparticles, and additional incorporation of PLURONIC surfactants L43, L44, and L61 further reduced the HI value of the microparticles.

Figure 5:
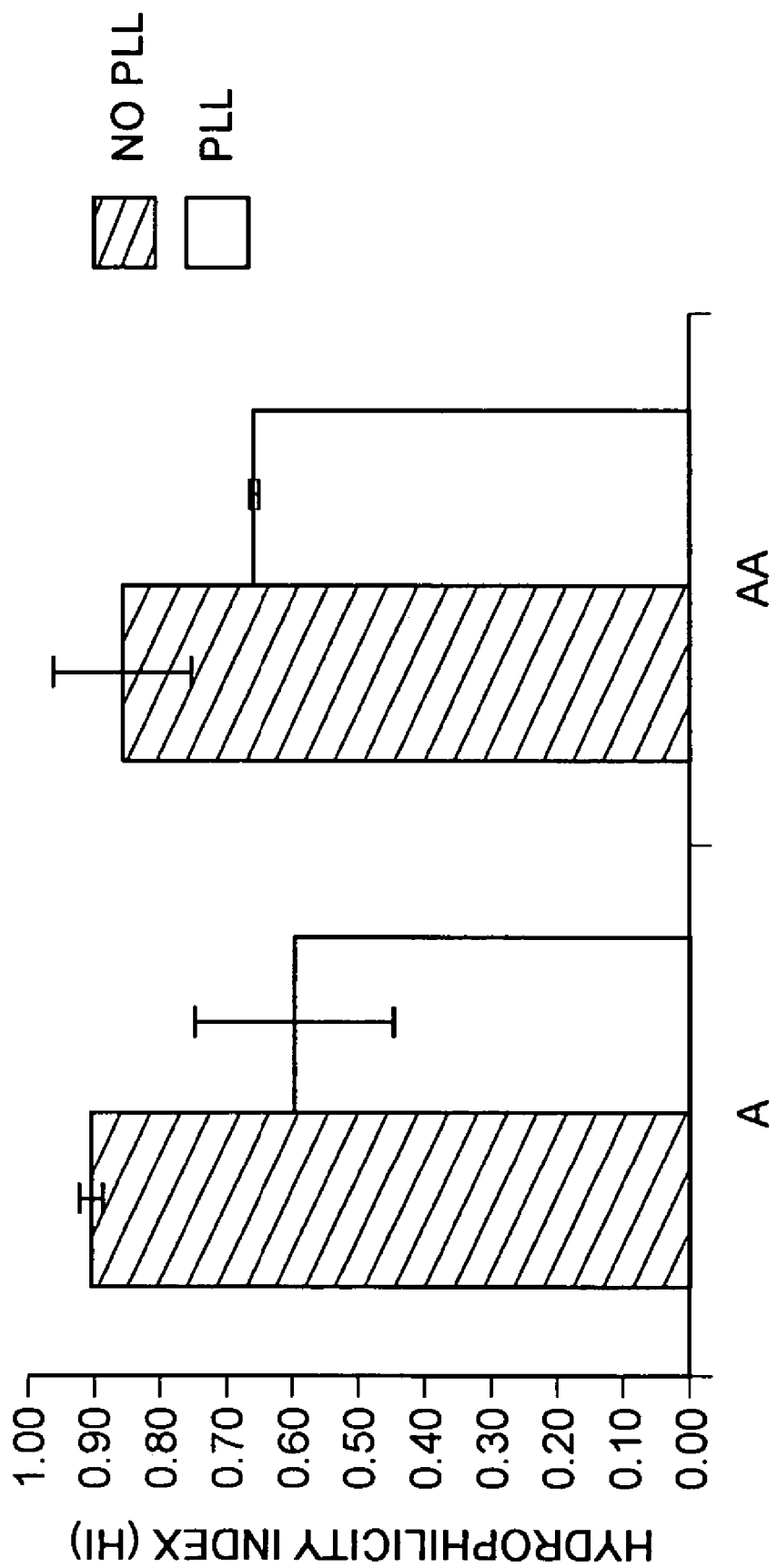

FIG. 5 shows the effect of PLL coating on the hydrophobicity of alginate microparticles, as measured by phase partitioning. Samples are labeled as in FIG. 1, and results are reported as mean values of three samples, with bars for standard deviations. PLL coating of microparticles made with the base formulation reduced the HI value from 0.90 to 0.59, and PLL coating of microparticles made with the base formulation plus methylcellulose resulted in a reduction of the HI value from 0.85 to 0.65.

Figure 6:
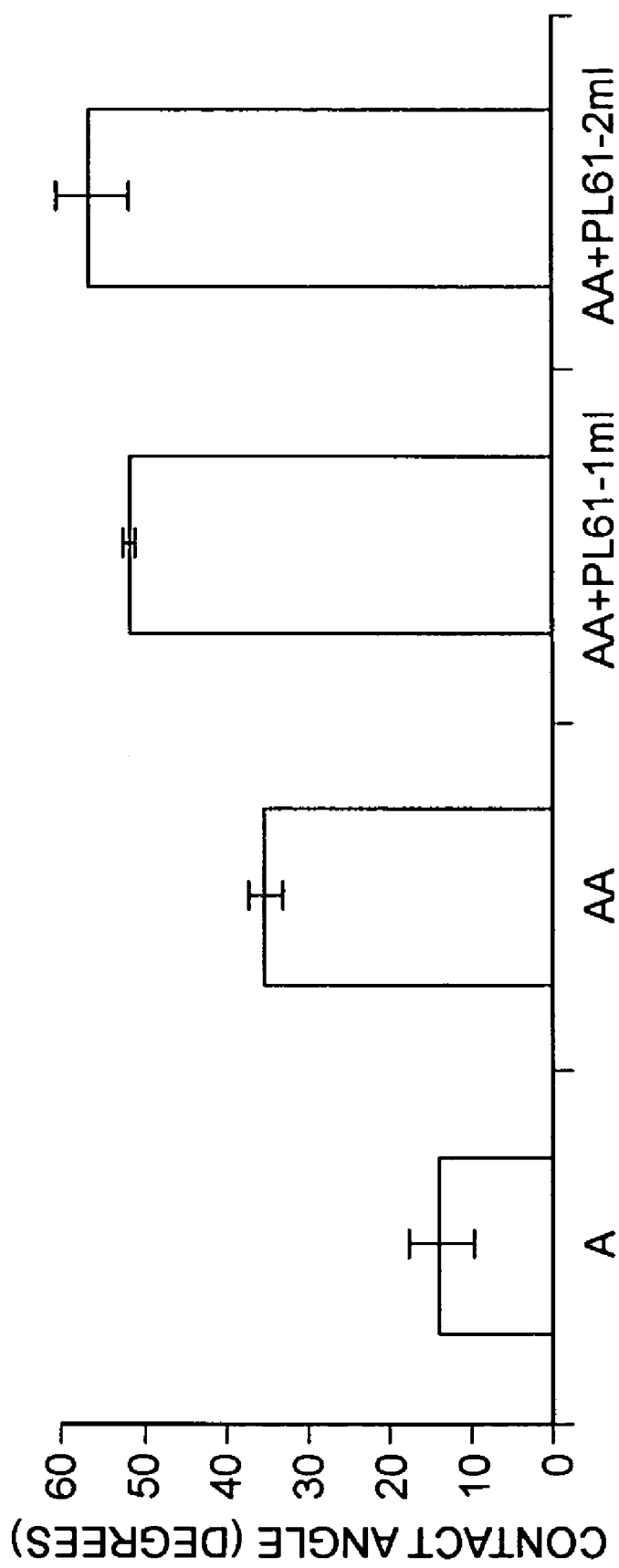

FIG. 6 shows the effect of METHOCEL A4C methylcellulose and PLURONIC L61 surfactant on the hydrophobicity of alginate microparticles, as measured by the contact angle measurement technique. Samples are labeled as in FIG. 1, and results are reported as mean values of five samples, with bars for standard deviations. Larger contact angles indicate greater hydrophobicity of the microparticles.

Example 2

Effect of Surfactant Types and Crosslinker Cations on Loading Efficiency and Immune Response Microparticles were produced using a water-in-oil emulsion technique using 1.5% (w/v) sodium alginate (KELTONE HV, Monsanto Co.) which was mixed with ovalbumin (OVA) (Grade V, Sigma-Aldrich, Inc.) for immunogenicity studies, and fluorescein isothiocyanate-labeled bovine serum albumin (BSA-FITC, 25 mg/ml stock solution, Sigma-Aldrich, Inc.) for loading efficiency studies. Each antigen was individually mixed with alginate followed by the addition of surfactant in canola oil. BRIJ 93 (0.67 ml/batch, when used), TWEEN 85 (0.9 ml/batch, when used), and SPAN 85 (0.9 ml/batch, when used) (ICI Americas, Inc.) were the surfactants used in this study.

A water-in-oil emulsion was produced by a high-speed mixer method. A 1.5% (w/v) sodium alginate solution (8 ml/batch) and an antigen solution (2 ml/batch) were placed in a beaker and mixed for 2 minutes at 550 RPM using a Servodyne Mixer (Cole Palmer, Niles, Ill.). When using TWEEN 85 and SPAN 85 surfactants, the specified amount was placed on top of the alginate/antigen mixture; BRIJ 93 surfactant was added to the oil phase. Canola oil (40 ml/batch; and BRIJ 93, when used) was then added to the beaker containing the aqueous phase and mixed at 5,000

RPM for 1 minute. A divalent cation solution (8 ml/batch) was added while the emulsion was stirred at 5,000 RPM using a high speed mixer (SERVODYNE Model 50000-40, Cole-Parmer). Cation solutions used included 0.5% (w/v) CaCl, 10% (w/v) ZnCl$_2$; 1.25% (w/v) CaCl$_2$ and 5% (w/v) ZnCl$_2$ together; 2.5% (w/v) AlSO$_4$; and 2.5% (w/v) BaCl$_2$. Microparticles were harvested by centrifugation, washed twice in SDDW, once in 70% ethyl alcohol, followed by another wash in SDDW, and suspended in an equal amount, by weight, of SDDW.

Some samples were coated with poly-1-lysine (PLL) (MW 158,000 Daltons, Sigma-Aldrich, Inc.). To coat, microparticles were suspended by creating a vortex in a 50 ml conical polypropylene tube. An equal amount, by volume, of PLL was added dropwise to the microparticles while mixing. The microparticles were then allowed to mix for 30 minutes, then washed twice in SDDW to remove unreacted PLL, and then stored in SDDW until used.

To determine loading efficiency, microparticles containing BSA-FITC were mixed in a ratio of 1:3 v/v with 5% sodium tetrapyrophosphate (TSP) in a 96 well plate and incubated at room temperature in a humid chamber overnight. Each sample was tested in triplicate wells. The plate was centrifuged at 800 times gravity for 15 minutes, and 100 microliters ($\mu$L) of supernatant was then transferred to a flat bottom 96 well ELISA plate. The absorbance of each well was determined using a microtiter plate fluorometer (Model 7620, Cambridge Technology) with excitation at 485 nanometers (nm) and emission at 530 nm. A standard curve was generated by serial dilutions of known concentrations of BSA-FITC diluted in TSP. The mean absorbance for each sample minus background (TSP only) was interpolated from the standard curve to determine the amount of BSA-FITC loaded into each sample. This was divided by the amount of BSA-FITC mixed in alginate to determine a ratio of efficiency of loading.

Female twelve week old BALB\c mice were used in this study, with eight mice per experimental group. Mice were kept under standard husbandry conditions with food and water ad libitum.

A 250 $\mu$L dose of the microparticle suspension was injected subcutaneously (SC) in the cervical area at zero, three, and six weeks. The same volume of microparticle suspension was administered orally by gavage using a feeding needle to different mice at zero, one, and two weeks. Each dose was expected to contain 25 micrograms ($\mu$g) of OVA. ELISA assays showed that actual loading was 10 nanograms (ng) OVA per dose. Blood was collected from the orbital sinus at weekly intervals beginning at week two and concluding one week after the final inoculation. Serum was collected and frozen at $-70°$ C. until assayed. All mice were euthanized after the final blood sample was collected, and then intestinal explants were cultured 24 hours in RPM1-1640 plus 2× antibiotics (penicillin, streptomycin, and amphotericin B) plus 10% fetal calf serum in 12 well tissue culture plates. Four tissues were cultured for each mouse. At 24 hours, the plates were frozen at $-20°$ C. until assayed. Prior to assay, the plates were centrifuged at 800 times gravity for 10 minutes and supernatants were pooled for each mouse.

High binding ELISA plates (Costar) were coated with 100 $\mu$L of OVA diluted in carbonate-bicarbonate buffer (pH 9.6) at 15 $\mu$g/well overnight at 4° C. The plates were then washed once in SDDW, and then TRIS buffered saline with TWEEN 20 surfactant containing 10% normal goat serum (TBST-GS) was added to each well. Plates were then incubated at 37° C. for 1 hour, then washed two times with SDDW, and then serum samples were added. Mouse serum was diluted 1:100 in TBST-GS. Plates were then incubated for 1 hour at 37° C., washed five times, and appropriate dilutions of horseradish conjugated goat anti-mouse isotype antibody were added. Plates were then incubated for 1 hour at 37° C., followed by six washes. The substrate ABTS (Kirkegaard and Perry Laboratories) was added, and plates were incubated at room temperature until adequate color developed (45 minutes). Acid/alcohol (50 $\mu$L) was added to each well to stop the reaction and the absorbance of each well was determined using a microtiter plate reader (Model 3550, Bio-Rad Co.) at 450 nm. The mean absorbance for each group was determined for each antibody isotype. Supernatants of intestinal explants were evaluated in a similar manner but at a dilution of 1:2.

Figure 7:
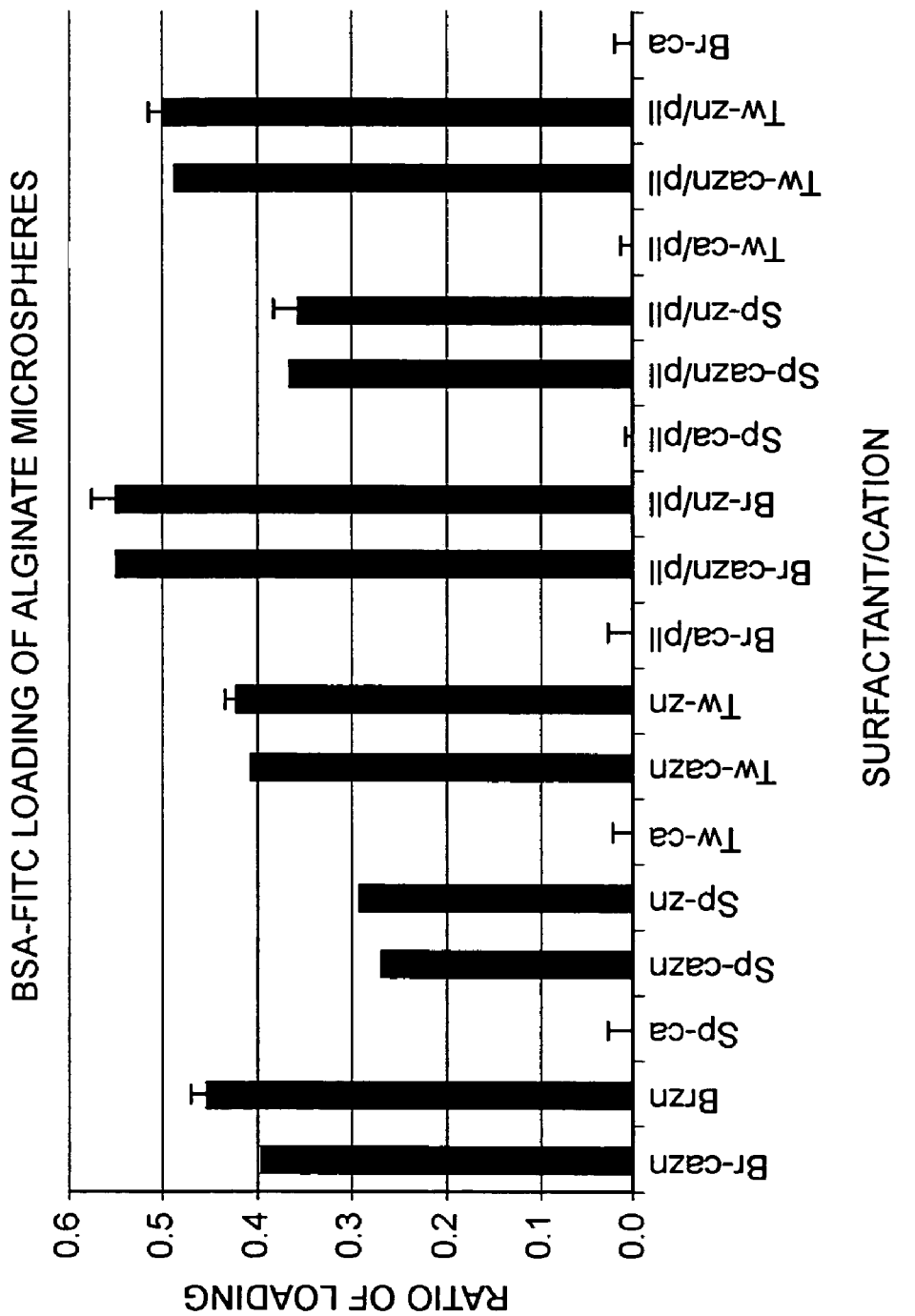

FIG. 7 shows the effect of various cation solutions and surfactants on loading efficiency. Abbreviations Br, Sp, and Tw denote use of BRIJ, SPAN, and TWEEN surfactants, respectively; ca denotes use of CaCl$_2$ crosslinker; zn denotes ZnCl$_2$ crosslinker; cazn denotes use of a mixture of CaCl$_2$ and ZnCl$_2$ crosslinker; pll denotes poly-1-lysine coated microparticles. Results are reported as mean values of six replicates, with bars for standard deviations. Loading of antigen using CaCl$_2$ alone was negligible. ZnCl$_2$ alone resulted in the greatest loading efficiency for microparticles not coated with poly-1-lysine. Using BRIJ 93 and TWEEN 85 surfactants resulted in similar loading efficiencies, while using SPAN 85 surfactant resulted in a comparatively lower loading efficiency. Poly-1-lysine coating resulted in higher loading across all samples.

Figure 8:
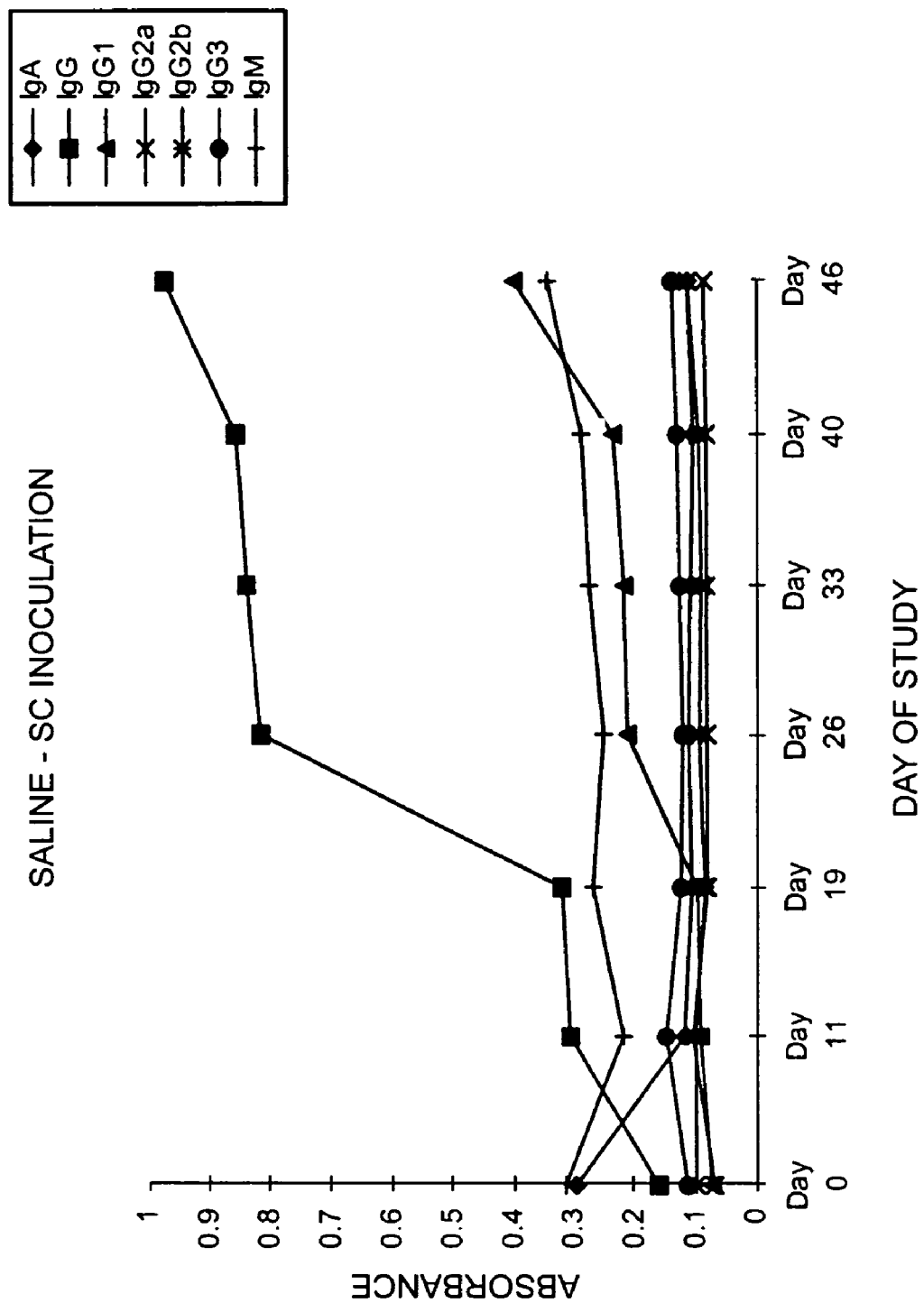
Figure 9:
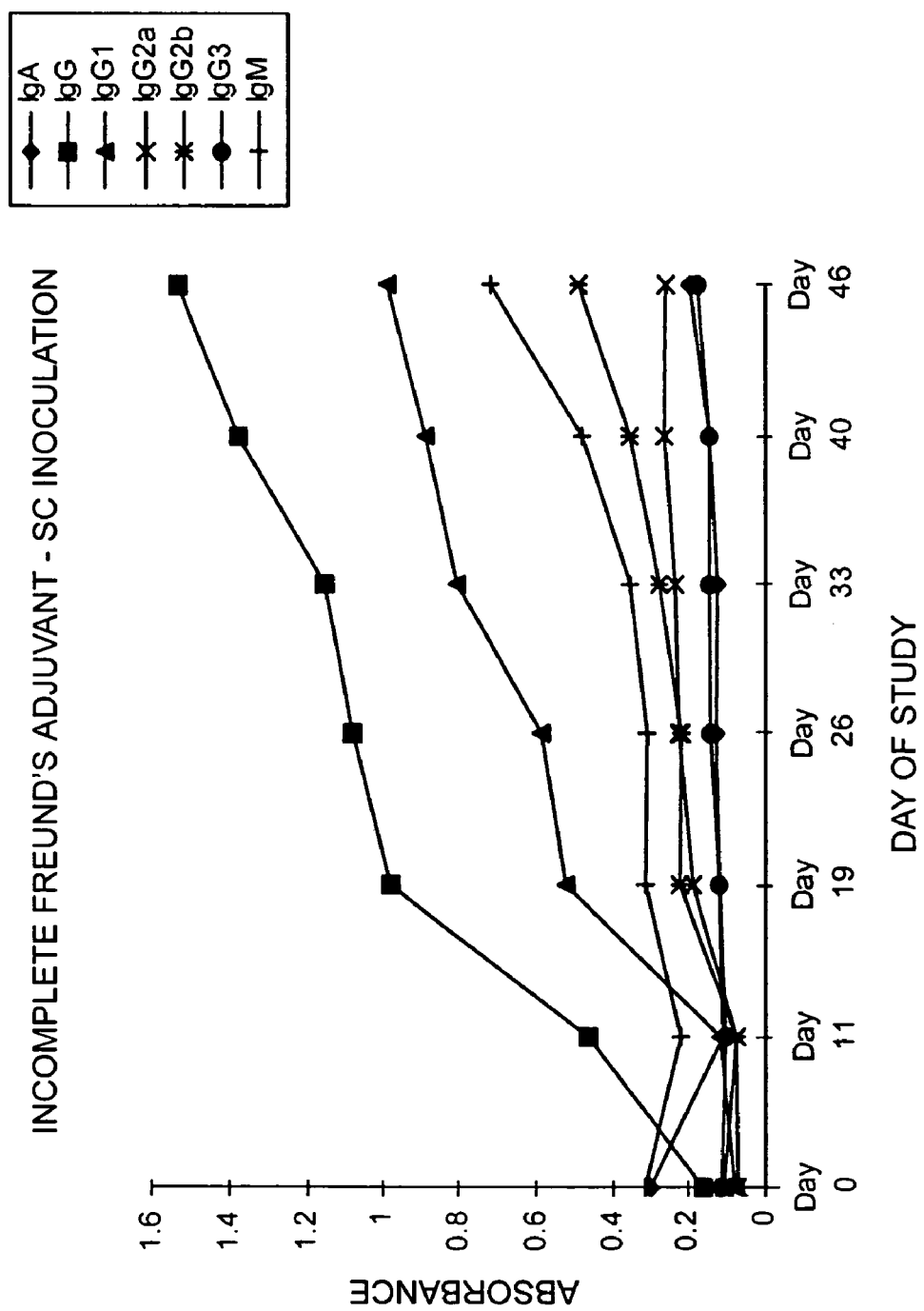
Figure 10:
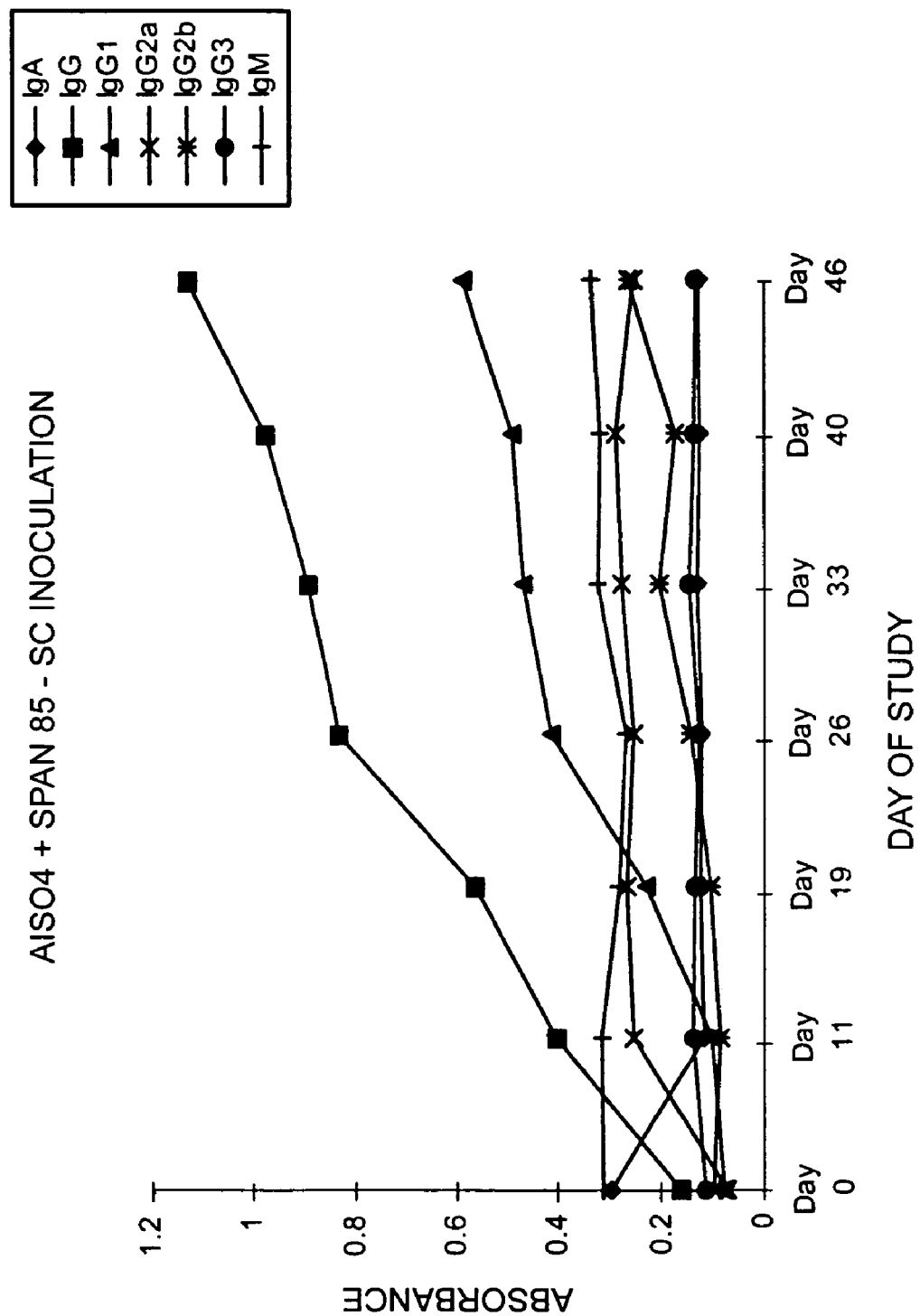
Figure 11:
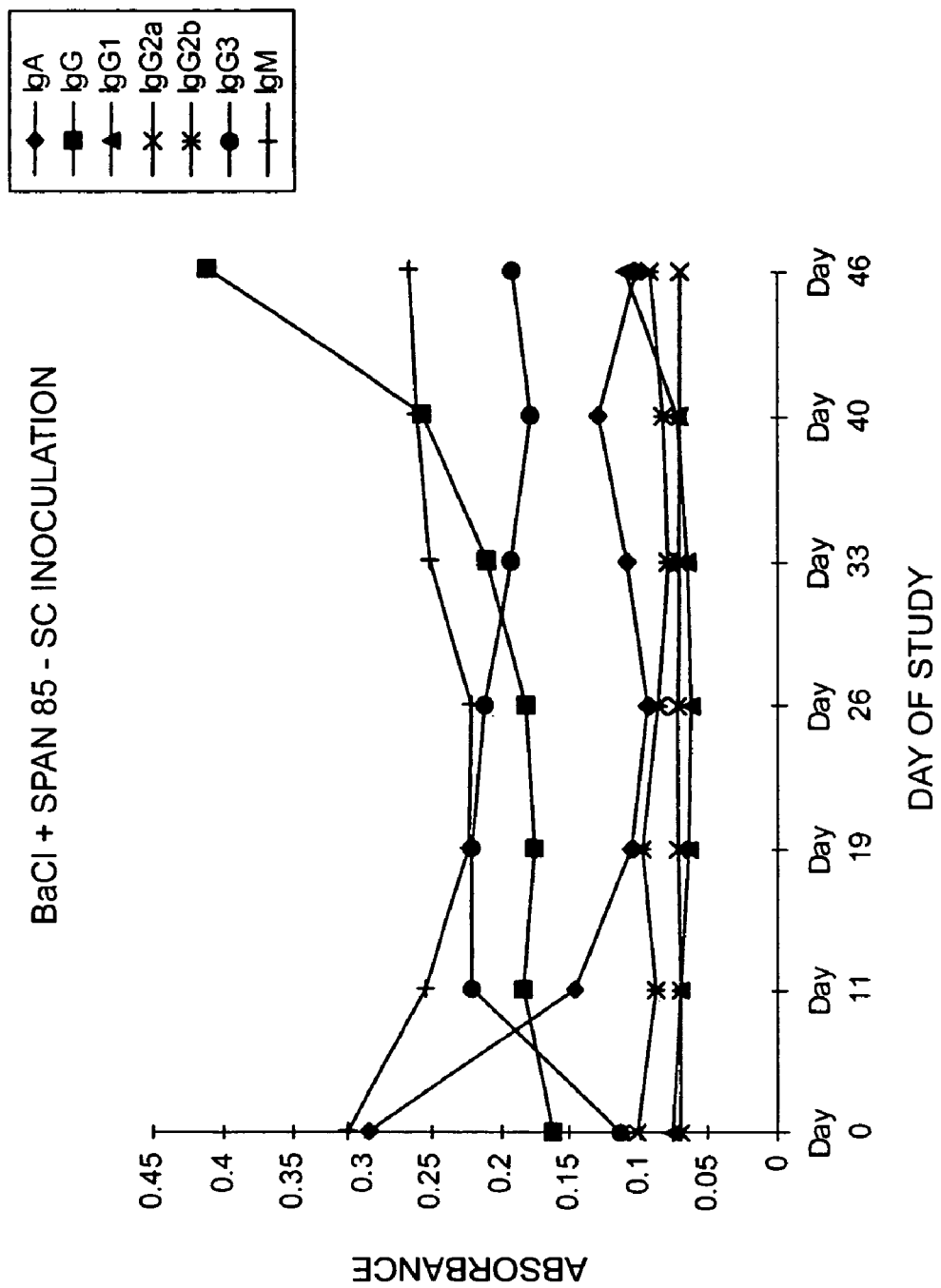
Figure 12:
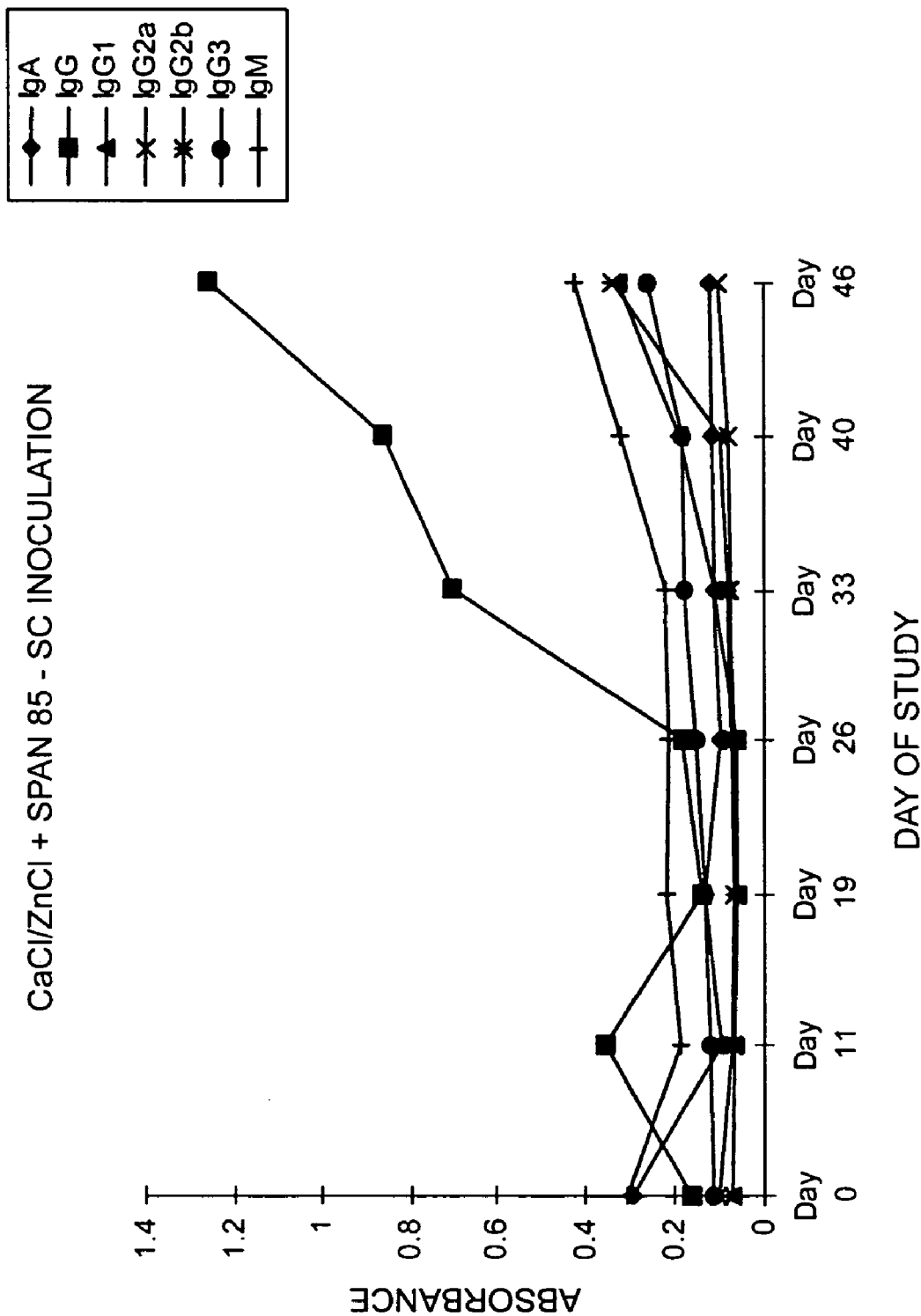
Figure 13:
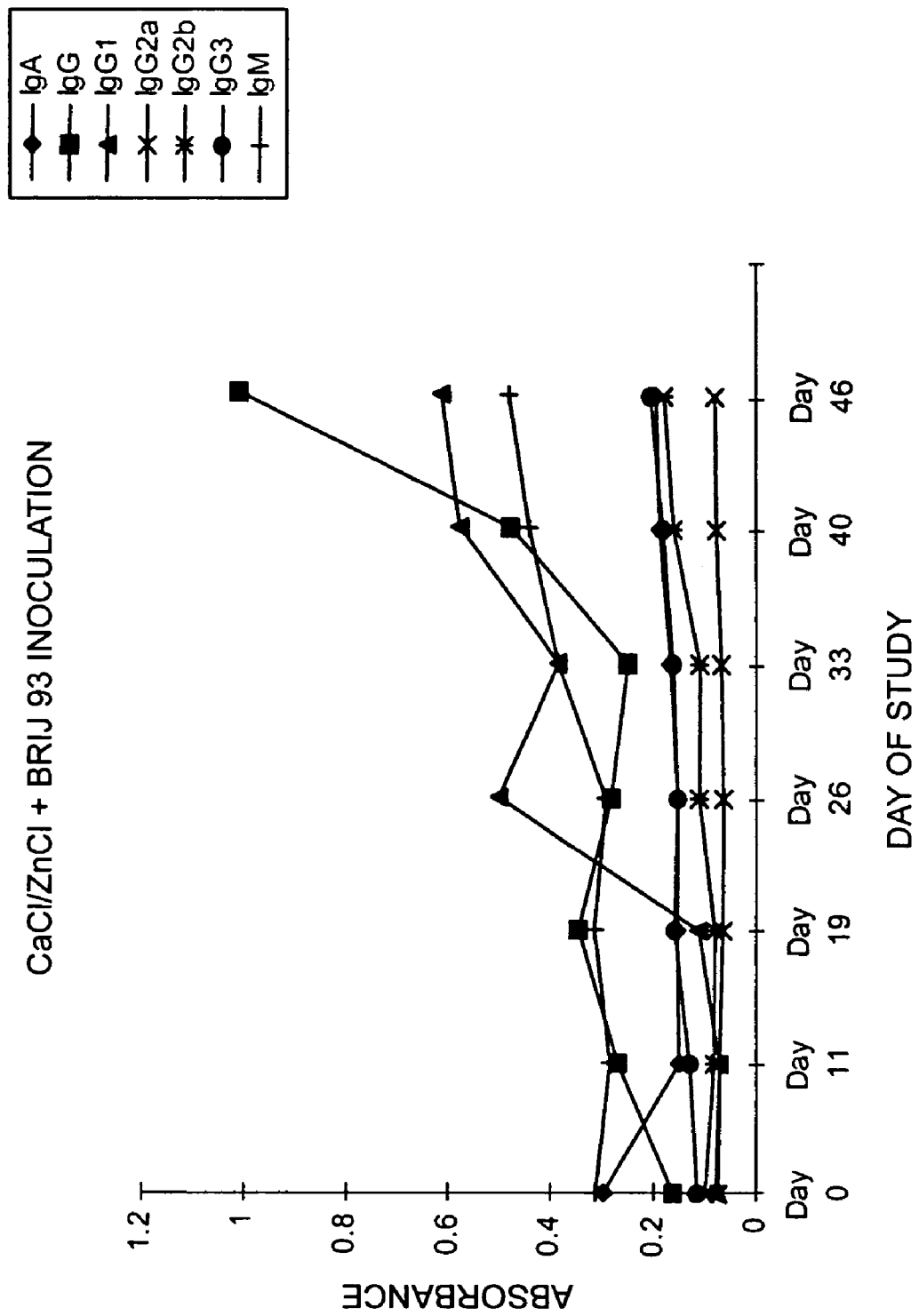
Figure 14:
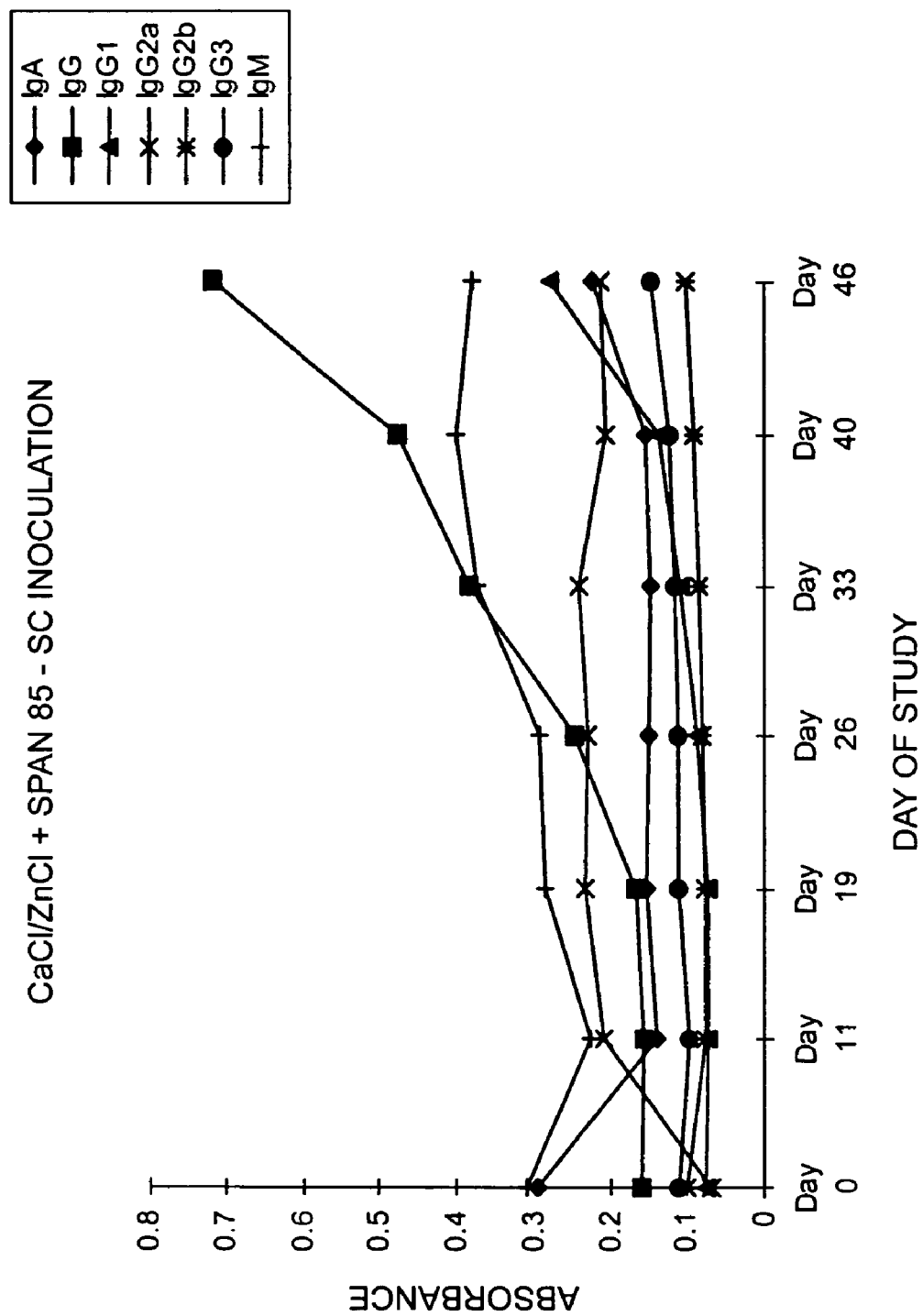
Figure 15:
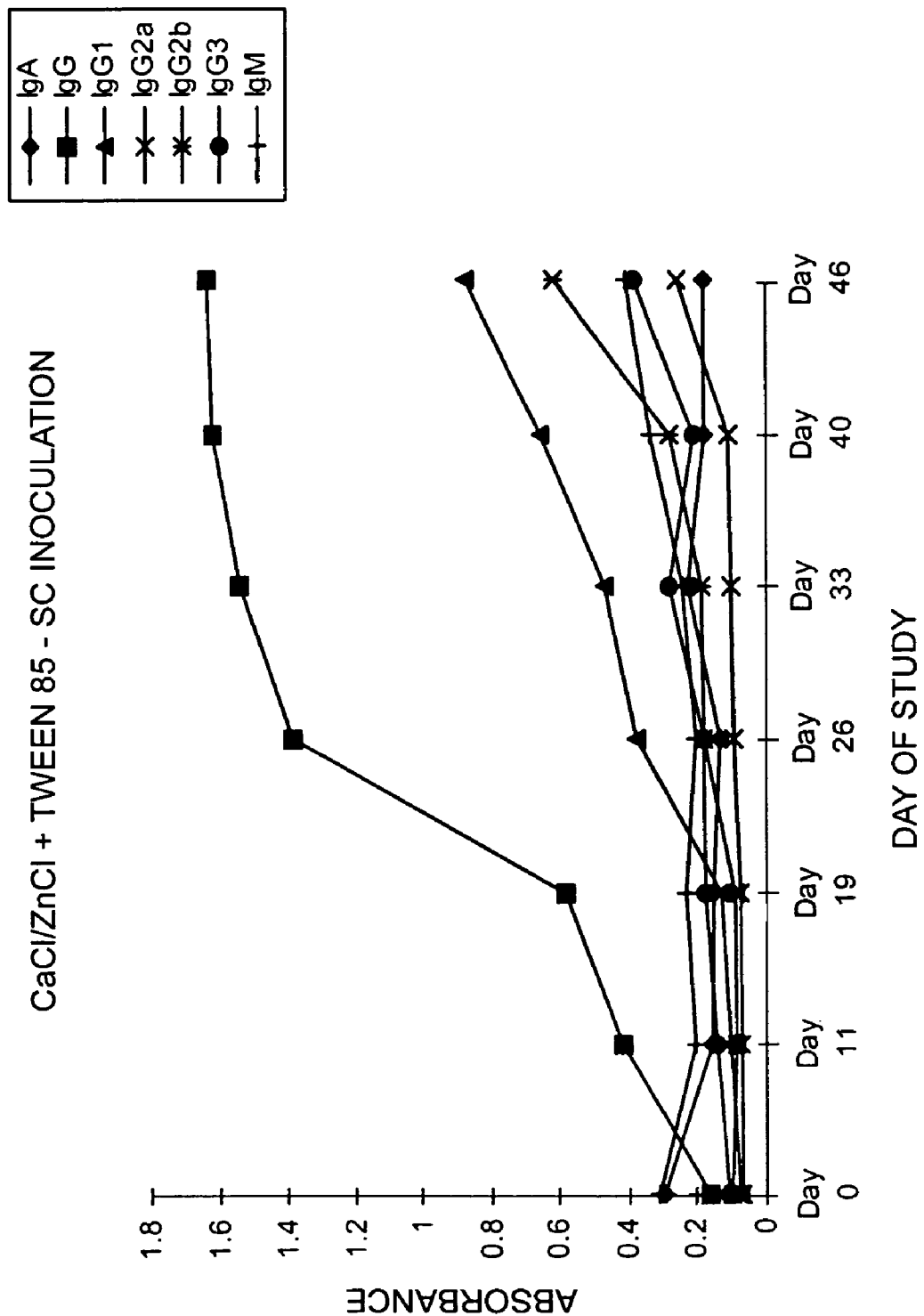
Figure 16:
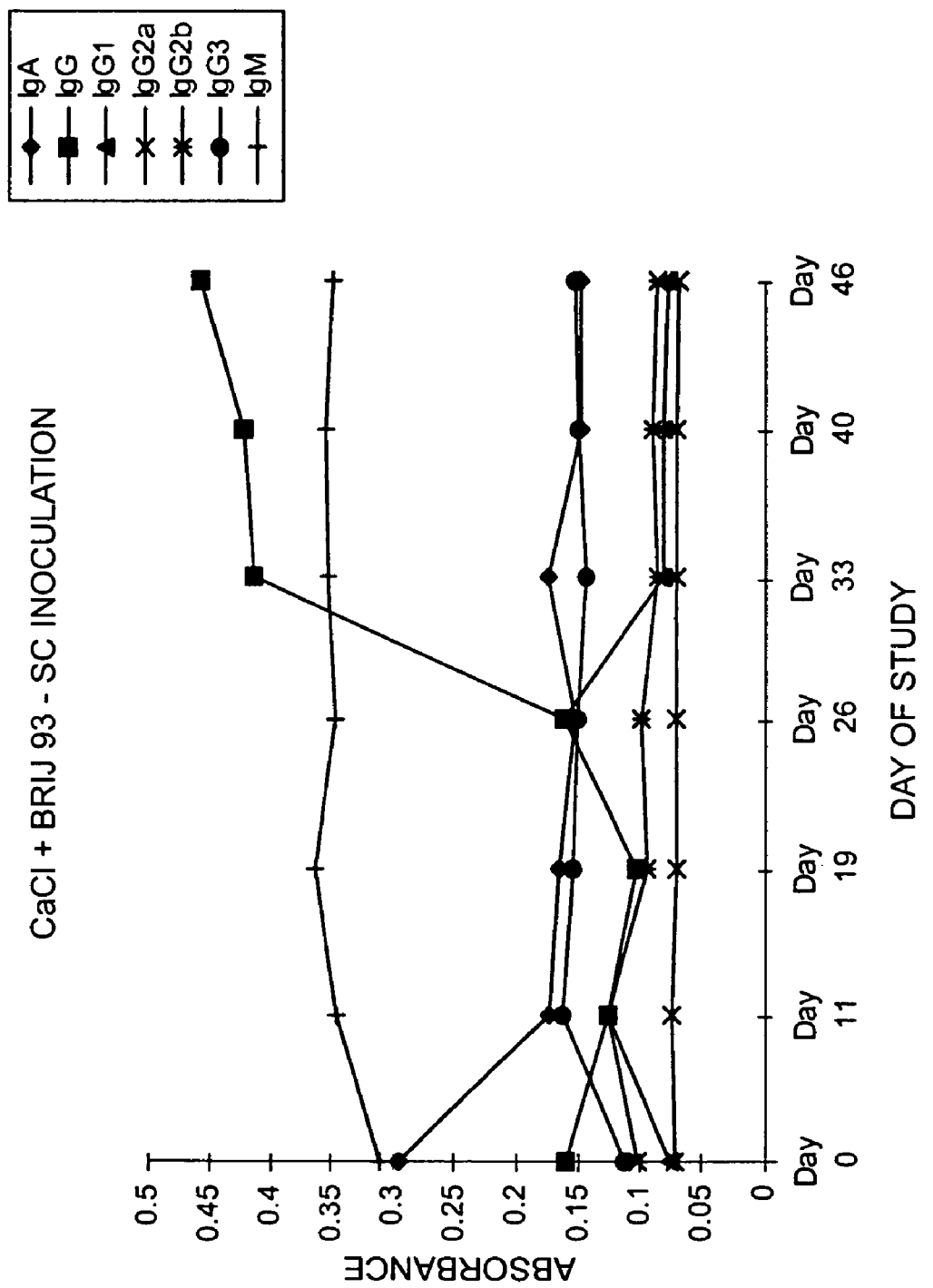
Figure 17:
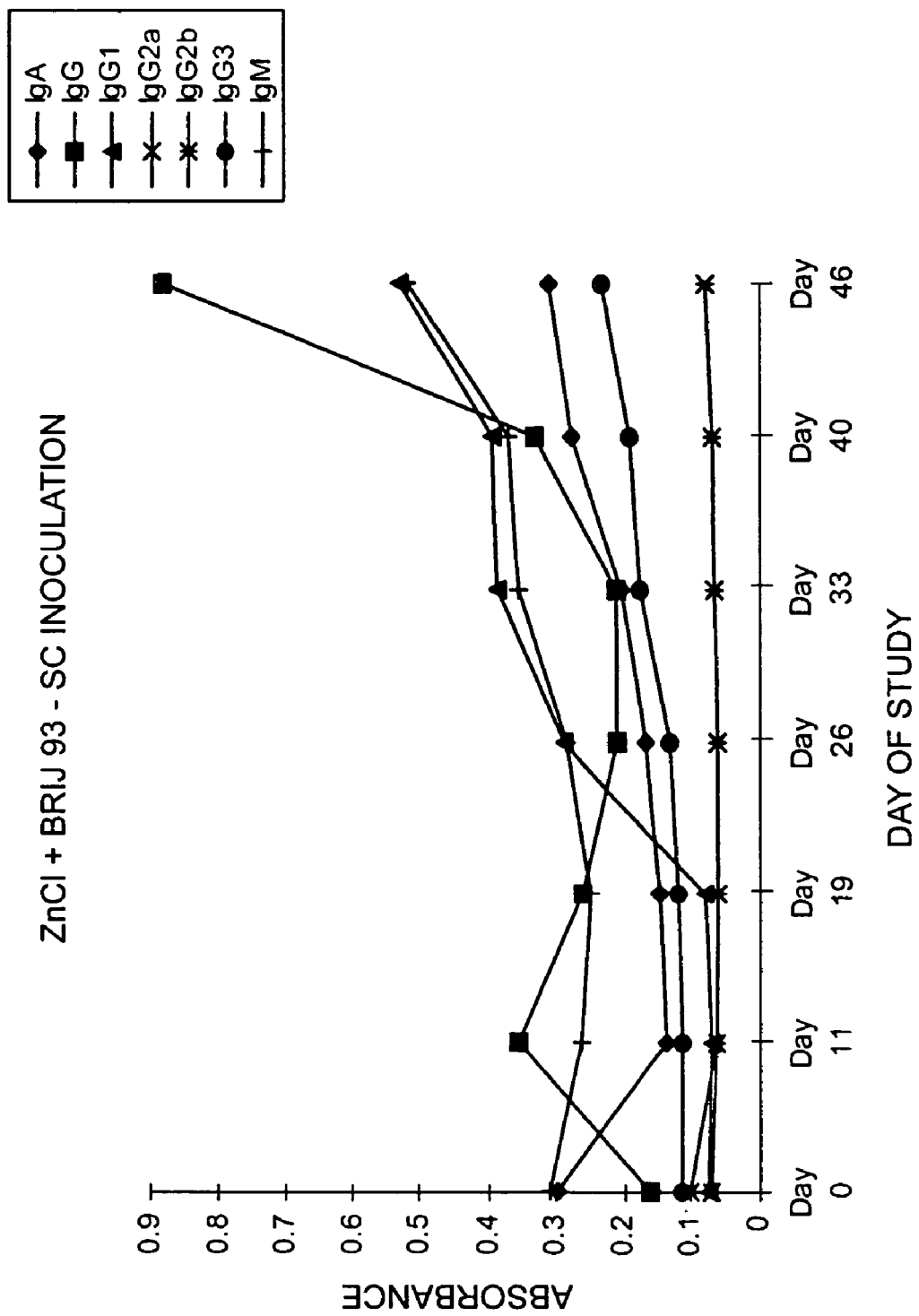

FIGS. 8 to 17 show antibody titer results of mice injected SC with microparticles containing ovalbumin. FIG. 8 shows the results for unencapsulated ovalbumin in saline. Microparticles made with CaCl$_2$ or BaCl$_2$ in the crosslinker solution showed increased IgG antibodies after the second inoculation, even though loading efficiency as determined by an ELISA trap assay determined the OVA load to be only 10 nanograms. Similar studies in loading efficiency with BSA-FITC in FIG. 7 confirmed that microparticles made with CaCl$_2$ had negligible protein present. Microparticles made with AlSO$_4$ had the earliest immune response, with IgG antibody titers increased by day 11 after the first inoculation. The profile of the immune response was similar to that of mice inoculated with OVA adjuvanted with incomplete Freund's adjuvant (IFA), although the magnitude of the response was greater with IFA. Microparticles made with BRIJ 93 as the surfactant tended to have delayed immune responses, until later in the study at day 33 or 40, whereas SPAN 85 and TWEEN 85 surfactants both produced earlier increases in antibody titers. The greatest effect due to surfactant was with TWEEN 85 surfactant, which showed an earlier and greater immune response with CaCl$_2$ and ZnCl$_2$ in the crosslinker solution, compared to microparticles made with either BRIJ 93 or SPAN 85 surfactants.

Intestinal explants showed low (absorbance value of 0.150 to 1:1 dilution) but significant increases in antibody titers to OVA. IgA values to OVA for samples made with BRIJ 93 surfactant with CaCl$_2$, SPAN 85 surfactant with AlSO$_4$ and BaCl$_2$, TWEEN 85 surfactant with ZnCl$_2$ and CaCl$_2$, ZnCl$_2$ alone, microparticles alone, and cholera toxin plus OVA, all had p values less than 0.05 compared to unencapsulated oral OVA. IgG values to OVA for BRIJ 93 surfactant with ZnCl$_2$, TWEEN 85 surfactant with ZnCl$_2$ and CaCl$_2$, and TWEEN 85 surfactant with ZnCl$_2$, and IgG2b values for all groups except SPAN 85 surfactant with AlSO$_4$, SPAN 85 surfactant with ZnCl$_2$, and microparticles only, had p values less than 0.05 compared to values for groups vaccinated with unencapsulated oral OVA. Microparticles made with $ZnCl_2$ alone or $ZnCl_2$ with $CaCl_2$ (and BRIJ 93 as surfactant) had a slower onset of immune response as the proportion of $ZnCl_2$ increased. The results show that the type of surfactant and type of cation affect the efficiency of loading of antigen and the immunogenicity of the microparticles.

The results show that microparticles exert an adjuvant-like effect with immune responses greater than antigen injected without adjuvant, and delayed release of antigen in some cases. The adjuvanticity of alginate microparticles of the invention is also suggested by the immune response seen in mice, despite detection of only low nanogram amounts of antigen in the microparticles. The adjuvanticity depends on the surfactant used and on the cation used, as shown in some cases in which, even with poor loading, antigen in microparticles in extremely low doses still induced an increase in antibody titer. Attempts of oral administration of these preparations did not result in detectable serum antibody titers. However, the ELISA assay could not confirm anything but low (less than one μg) amounts of protein present in these preparations—lower than known to be immunogenic for antigen within microparticles.

Example 3

Effect of PEO-PPO-PEO Surfactants, Poly(Propylene Glycol), and Methylcellulose on Properties of Alginate Microparticles A 1.5% (w/v) solution (8 ml/batch) of sodium alginate (400 cP viscosity; Acros Organics) was made. TWEEN 85 surfactant was added to the oil phase of each sample at 4 ml/batch. Methylcellulose was added to the alginate solution to a final concentration of 0.5% in some cases. PLURONIC surfactants (2 ml/batch, when used) and poly(propylene glycol) (2 ml/batch; MW 3,500 Daltons, Sigma-Aldrich, Inc.) were added to the oil phase (40 ml/batch canola oil, purchased from a local grocery store). The alginate solution and bovine serum albumin (BSA) were mixed with the oil. Alginate microparticles were made by the emulsion crosslinking technique described in Example 1, using an 8 ml mixture of calcium acetate and zinc acetate (4 ml of 4.2% (w/v) calcium acetate, EM Science, Gibbstown, N.J. and 4 ml of 9.8% (w/v) zinc acetate, Sigma-Aldrich, Inc.) as a crosslinking solution.

Microparticle size was measured using an ACUSIZER 770 optical particle sizer equipped with an autodiluter system (Particle Sizing Systems, Inc.). A 10 times dilution (by volume) of the original microparticle suspension was made in SDDW. Size was determined before and after 16 cycles of sonication (Branson Sonifier 450; 40% of duty cycle of 60 Hz for 15 seconds per sample).

Loading efficiency was determined using a micro BCA assay kit (Pierce), by the method described in Example 2.

Microparticle hydrophobicity was evaluated by the phase partitioning technique described in Example 1 using a 3.5 mg/ml microparticle suspension as the aqueous phase.

Figure 18:
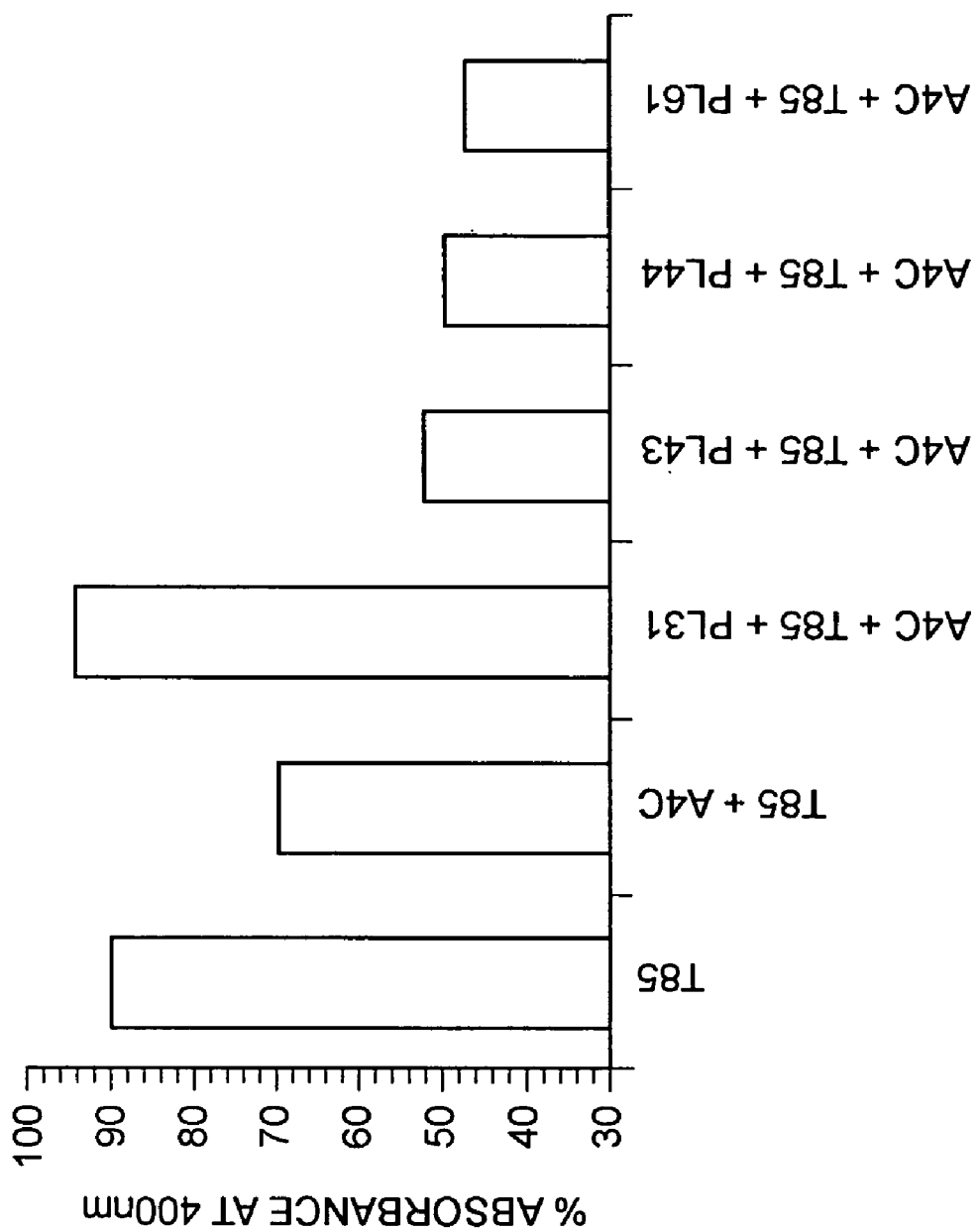

FIG. 18 shows the effect of adding the various PEO-PPO-PEO copolymer (PLURONIC) surfactants and methylcellulose (A4C) to a base alginate formulation with TWEEN 85 surfactant (T85) on the hydrophobicity of alginate microparticles. PLURONIC surfactant L31 was found to significantly decrease hydrophobicity of microparticles made with methylcellulose, whereas PLURONIC surfactants L43, L44 and L61 greatly enhanced hydrophobicity. Previous work (unpublished) showed that PLURONIC surfactant L81 decreased hydrophobicity and methylcellulose increased hydrophobicity of alginate microparticles.

The surfactant HLB has a bearing on the hydrophobicity of the microparticles. When a surfactant with HLB of ≦5.0 was used, yield (pellet weight) was significantly lower (about 50% lower than usual). However, when a surfactant with HLB of 7–9 was used, yield and loading efficiency were comparable to results using a surfactant with HLB of 11 (TWEEN 85 surfactant alone).

Figure 19:
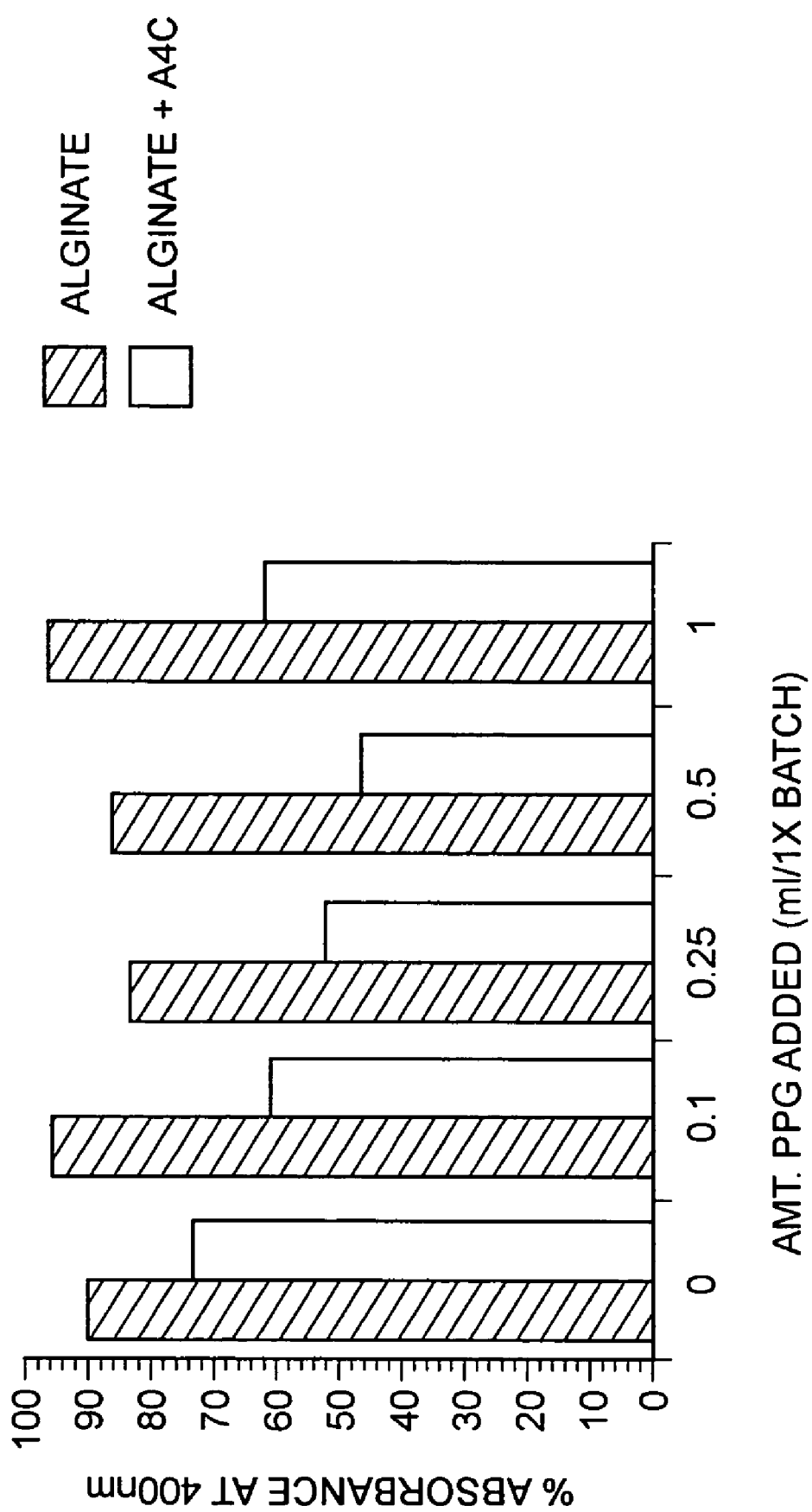

In some samples, PPG was added to the oil phase and thoroughly mixed before adding alginate. Hydrophobicity was evaluated by the n-octane/water partitioning technique. FIG. 19 shows the effect of PPG on alginate microparticle hydrophobicity. Hydrophobicity of alginate microparticles made with methylcellulose increased with increasing PPG concentration up to 0.5 ml/1× batch. Higher concentrations of PPG decreased particle hydrophobicity. PPG did not affect the hydrophobicity of microparticles made with alginate alone, which suggests interaction between the hydrophobic PPG molecule and methylcellulose.

Table 2 shows the effect of PPG on alginate microparticle size and BSA loading efficiency. Particle size did not change significantly with the addition of PPG. In general, particle size is larger with PPG than with PLURONIC surfactants. BSA loading efficiency of microparticles made with PPG is comparable to those made with PLURONIC surfactants.

TABLE 2

| Vol. PPG (ml/1X batch) | Pellet wt. (gm) | Loading eff. (%) | Size (μm) no sonication | Size (μm) 16 cycles sonication |
|---|---|---|---|---|
| 0 | 3.33 | 52.84 | 14.65 | 7.47 |
| 0.1 | 4.48 | 79.8 | 27.21 | 13.3 |
| 0.25 | 3.82 | 75.8 | 21.0 | 8.7 |
| 0.5 | 4.09 | 74.5 | 15.64 | 8.71 |
| 1.0 | 3.53 | 66.1 | 13.38 | 6.36 |
| 1.5 | 3.68 | 75.4 | 15.38 | 7.26 |
| 3 | 3.55 | 75.7 | 13.6 | 6.9 |

Example 4

Effect of PLL Coating on Microparticle Size

Microparticles were prepared by an emulsion technique using the method of Example 3, followed by coating with PLL (MW 25,000). To coat with PLL, microparticles were suspended in SDDW, sonicated 16 cycles, and added to an equal volume of 0.2% (w/v) PLL. The microparticles were vortexed thoroughly, and then placed on a shaker at 200 RPM at room temperature for 5 minutes. The microparticles were then centrifuged for 10 minutes to pellet, the pellet was washed once with SDDW, and then resuspended 1:1 (w:w) in SDDW.

Figure 20:
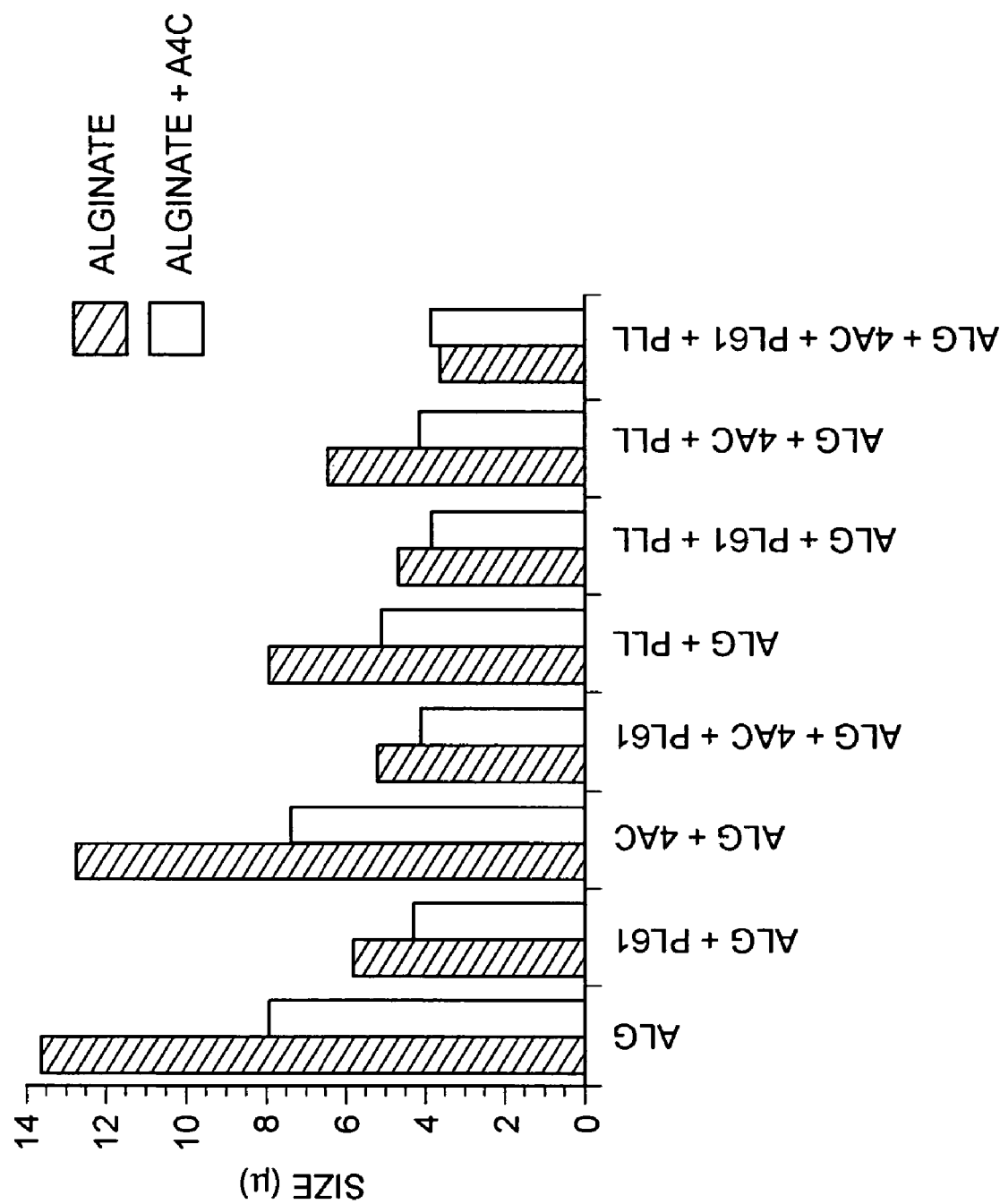

As shown in FIG. 20, coating the microparticles with PLL resulted in a smaller mean volume size of the microparticles. This may be due to coating of smaller microparticles making them "visible" to the particle analyzer, which ignores microparticles less than 1 μm in diameter. Alternatively, it may be due to an increased positive charge of the hydrophobic microparticles, making them less likely to clump or be attracted to each other.

Example 5

Effect of Formulation Variables on Immune Response in Mice Following Oral Administration of Antigen-loaded Alginate Microparticles Alginate microparticles were produced using one of two surfactant formulations. The first contained only alginate and TWEEN 85 surfactant. The second formulation contained alginate, TWEEN 85 surfactant, METHOCEL A4C methylcellulose, and PLURONIC L61 surfactant.

Two antigens were used for alginate microparticle loading: (1) the unadjuvanted portion of the commercial *Pasteurella haemolytica* leukotoxoid/bacterin ONE-SHOT (Pfizer Inc., Exton, Pa.), rehydrated with sterile water to double the strength of the normal dilution (i.e., 50 ml of water instead of 100 ml of adjuvant was used to rehydrate the lyphilized product); and (2) outer membrane proteins (OMPs) of *P. haemolytica* purchased from Dr. Tony Confer of Oklahoma State University. Each antigen was encapsulated in microparticles separately, and the microparticles were then combined (50:50 on a weight basis) prior to vaccination.

Alginate microparticles were made by the emulsion crosslinking technique described in Example 1, with the exception that methylcellulose (when used) was added to the alginate solution to a final concentration of 0.25 wt. %, and 5× batch sizes were made. Formulations were prepared using the reagents and amounts tabulated below:

TABLE 3

| Component | Alginate + TWEEN 85 + OMP | Alginate + TWEEN 85 + A4C + PL61 + OMP | Alginate + TWEEN + ONE-SHOT | Alginate + TWEEN 85 + A4C + PL61 + ONE-SHOT |
|---|---|---|---|---|
| Alginate (1.5 wt. %) | 40 ml | | 40 ml | |
| Alginate (1.5 wt. %) + A4C (0.32 wt. %) | | 40 ml | | 40 ml |
| TWEEN 85 | 20 ml | 20 ml | 20 ml | 20 ml |
| PLURONIC L61 | | 10 ml | | 10 ml |
| OMP (3.2 mg/ml) | 6.5 ml | 6.5 ml | | |
| ONE-SHOT (2 mg/ml) | | | 15.5 ml | 15.5 ml |
| SDDW | 8 ml | 5 ml | | |
| Canola Oil | 200 ml | 200 ml | 200 ml | 200 ml |
| Ca Acetate (4.2% (w/v)) + Zn Acetate (9.8% (w/v)) | 40 ml | 40 ml | 40 ml | 40 ml |

Orally vaccinated mice received their doses by gastric lavage using a stainless steel feeding needle. There were 8 different vaccination groups of mice.

Female BALB/c mice (8–12 weeks old) were used for this study. For each vaccination group, there were 30 mice in three blocks of 10 mice each. Each mouse in a group received the same vaccine at the same time. Each block of 10 mice was challenged with a different dose of bacteria. Three 10-fold dilutions of bacteria were used for each group. Following challenge, the percentage of death was determined for each block of mice for three different vaccination challenge doses of bacteria.

Mice vaccinated orally received one dose for 3 consecutive days, followed by a booster 4 days later. Mice vaccinated parenterally received one dose at day zero. All mice were challenged 5 weeks after the first inoculation. Challenge was administered as an intraperitoneal injection of the bacteria in tryptic soy broth plus 2% yeast extract. Each mouse received 200 μL of bacteria of either $10^{-6}$, $10^{-5}$, or $10^{-4}$ CFU/mouse. Mice were observed for 96 hours and daily deaths were recorded, with dead or dying mice removed daily. The percentage of mice that died per group was noted.

Figure 21:
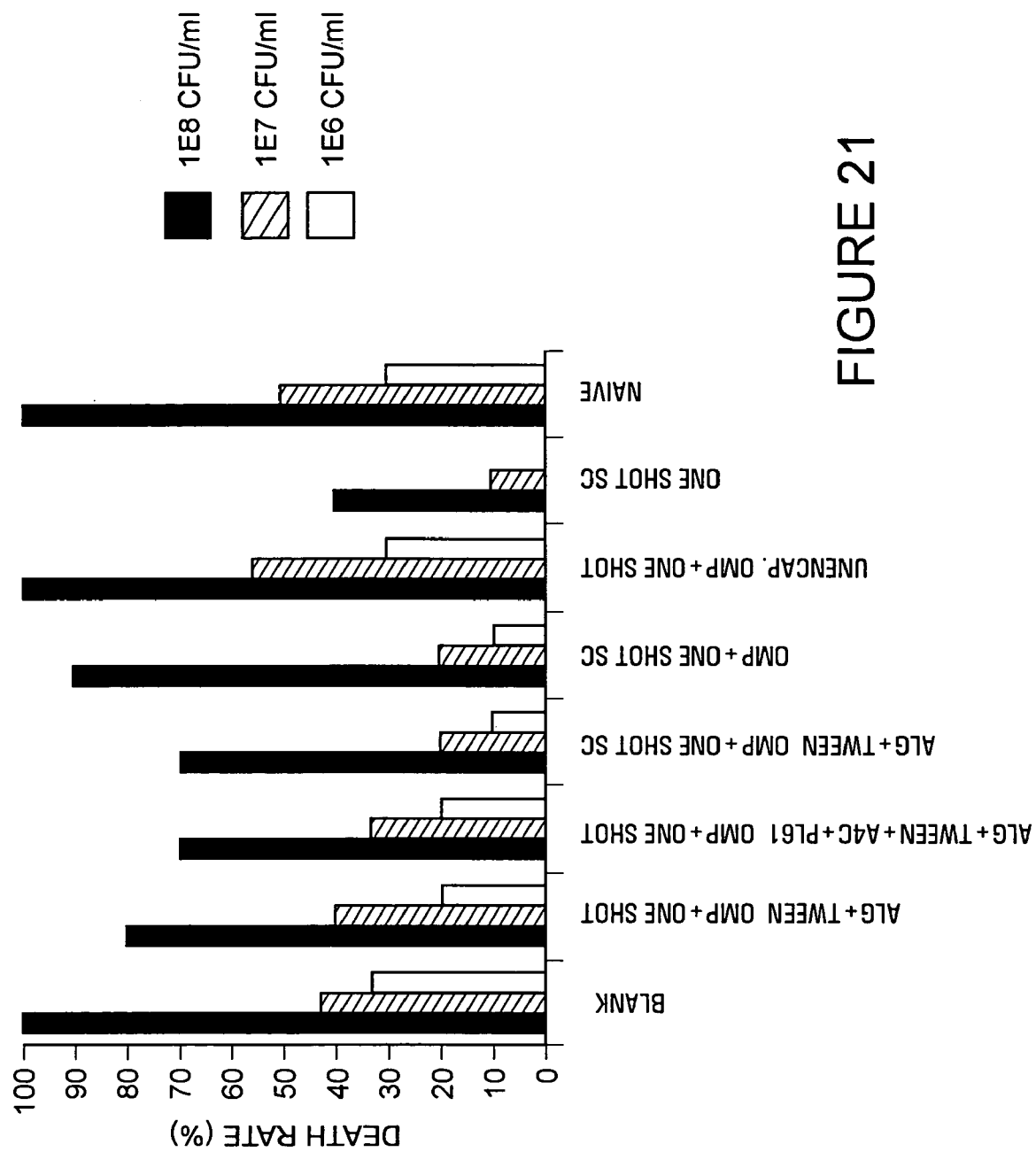

FIG. 21 depicts the mortality results for each vaccination group, wherein Blank=microparticles containing no antigen; Alg+TWEEN OMP+ONE SHOT=oral administration of antigen in simple alginate microparticle formulation with TWEEN 85 surfactant; Alg+TWEEN+A4C+PL61 OMP+ONE SHOT=oral administration of antigen in a more complex, hydrophobic formulation of microparticles using TWEEN 85 surfactant, methylcellulose, and PLURONIC L61 surfactant; Alg+TWEEN OMP+ONE SHOT SC=subcutaneous administration of alginate microparticles made using a simple formulation of alginate with TWEEN 85 surfactant; OMP+ONE SHOT SC=vaccine administered by subcutaneous inoculation of unencapsulated soluble antigens; Unencap. OMP+ONE SHOT=oral administration of unencapsulated soluble antigens; ONE SHOT SC=commercial adjuvanted unencapsulated vaccine given as directed (one dose) by subcutaneous inoculation into the neck; and Naive=non-vaccinated but challenged mice.

At the two highest challenge doses of bacteria (labeled "−1" (highest) and "−2") the group that received the oral vaccine had a slightly lower death rate than the mice vaccinated orally with blank (empty) microparticles. Both groups vaccinated orally with encapsulated vaccine had a lower death rate than naive mice or mice vaccinated orally with unencapsulated antigen. These data indicate a benefit to the encapsulation of orally administered vaccine. For both challenge doses, the mice vaccinated orally with the formulation of alginate microparticles that contained methylcellulose, PLURONIC L61 surfactant, and TWEEN 85 surfactant had a lower death rate than the group vaccinated orally with antigen in alginate with TWEEN 85 surfactant only.

The improved efficacy shown is most likely linked to the improved hydrophobicity of the microparticles. The smaller size and improved loading also may have added to the efficiency of the delivery of the antigens to the mice, although loading efficiencies were probably not sufficiently different to account for major differences in antigen loads delivered to these mice.

Example 6

Effect of Formulation Variables on Microparticle Properties, Cellular Uptake by Macrophages, and Cytotoxicity of Alginate Microparticles to Phagocytic Cells

Alginate microparticles were made by the emulsion-cross-linking technique. TWEEN 85 surfactant (Sigma-Aldrich) was used as a surfactant in all samples. A 1.5% (w/v) solution (8 ml/batch) of sodium alginate (400 cP viscosity; Acros Organics) was prepared in SDDW. Either methylcellulose (METHOCEL A4C) or hydroxypropyl methylcellulose (METHOCEL K3), when used, was added first to the alginate solution to a final concentration of 0.5% (w/v). TWEEN 85 (4 ml/batch, added to all samples), and PLURONIC surfactants (2 ml/batch, when used) (BASF Corp.) were added to the oil (40 ml/batch; canola oil; Meijer, Inc., Kalamazoo, Mich.).

To prepare alginate microparticles containing antigen, a solution containing bovine serum albumin (BSA) (2 ml/batch) was first mixed with the 1.5% (w/v) alginate (plus cellulose ether, when used) solution to a final concentration of 1 mg/ml. The water phase was subsequently added to the oil phase in a volume ratio of 1:4. An emulsion and then alginate microparticles were made by the methods described in Example 1 using a 8 ml solution of calcium and zinc acetate (4 ml of 4.2% (w/v) calcium acetate and 4 ml of 9.8% (w/v) zinc acetate) as the crosslinker.

Alginate microparticles were coated with PLL (Mol. Wt. 21,000 Daltons; Sigma-Aldrich, Inc.) by the method described in Example 1.

Particle size was measured using an ACUSIZER 770 optical particle sizer equipped with an auto-diluter system (Particle Sizing Systems, Inc. Santa Barbara, Calif.). A 10-fold dilution-(by volume) of the original microparticle suspension was made in SDDW. Three size determinations were made for each formulation and the mean value is reported.

Hydrophobicity for each alginate microparticle formulation was determined by measuring contact angle on a glass slide coated with microparticles by the method described in Example 1, except that no PLL coating of the glass slides was necessary for PLL coated microparticles.

Active confluent log phase culture of the U937 mouse macrophage cell line was used for the phagocytosis study. These cells closely resemble the M cells of the Peyer's patches. Cells were harvested and re-suspended at a concentration of $10^6$ cells/ml. Lipopolysaccharide (LPS, Sigma-Aldrich Inc. St. Louis Mo.) was added to the suspension to a final concentration of 10 μg/ml. Cells were collected after 48 h of incubation with LPS, and were then washed with RPMI 1640 medium (Life technologies, Grand Island, N.Y.). They were then transferred to a 24 well tissue culture plate at 0.5 ml/well ($10^5$ cells/ml). Cells were allowed to adhere to the bottom of the wells by incubating at 37° C. and 5% $CO_2$ for 4 h. Then 100 μl of alginate microparticle suspension (1:1 w:w in 0.9% (w/v) saline) or microparticle supernatant was added to each well. The plate was incubated at 37° C. and 5% $CO_2$ for 30 min. Supernatant as well as adherent cells were then collected. Cells were stained with propidium iodide (Sigma-Aldrich Inc., St. Louis, Mo.) in phosphate buffered saline and two-color-flow cytometry was performed.

Bovine blood was collected by venipuncture into a 50 ml syringe containing 1.5% EDTA (pH 6.8). The blood was then centrifuged at 1,000 times gravity for 25 minutes. The plasma buffer layer and the top few milliliters were discarded. The packed erythrocyte fraction was suspended in enough volume to suspend of 0.85% NaCl-phosphate buffer (pH 6.8), and 10 ml was placed in 20 ml of sterile water for 40 seconds to lyse the erythrocytes. Immediately thereafter, 10 ml of a 2.7% NaCl-phosphate buffer solution was added to restore isotonicity. The leukocytes, consisting of polymorphonuclear neutrophils (PMNs), were washed twice and suspended in hanks balanced salt solution (HBSS) with calcium and magnesium. PMNs were adjusted to a final concentration of $5 \times 10^6$ cells/ml in HBSS.

Cytotoxicity studies were carried out for the following formulations: alginate (A), alginate with methylcellulose (AA), AA with PLURONIC L61, with and with out PLL coating. Polystyrene microspheres (average diameter 2.9 μm, Sigma-Aldrich, Inc.) were used as a control. A one milliliter PMN suspension was centrifuged gently to pellet the PMNs. A one milliliter suspension of microparticles in HBSS was added to the pellet and gently vortexed to suspend PMNs. HBSS was added to the control tubes. Tubes containing the mixtures were incubated at 37° C. and 5% $CO_2$ for 3 h. A ten microliter suspension was taken and mixed with 10 μL of Trypan blue. A ten microliter sample of that mixture was placed on a hemacytometer, and dead and living cells were counted, and percentage of viable cells was recorded to compare toxicity of each formulation.

Figure 22:
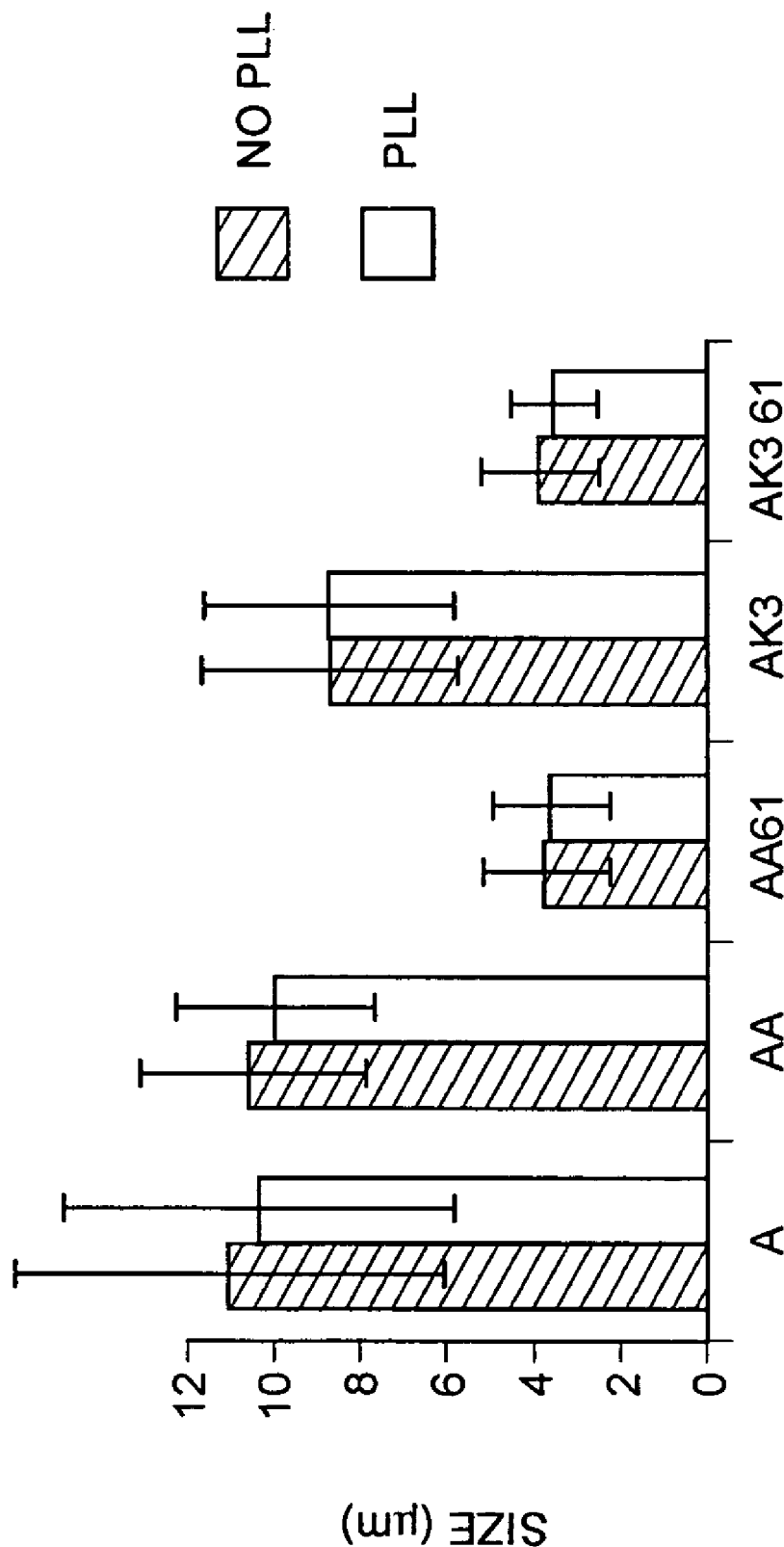

FIG. 22 shows the effect of various alginate microparticle formulations on the mean volume size of alginate microparticles. The five formulations examined were alginate (A), alginate with methylcellulose (AA), AA with PLURONIC L61 surfactant (AA61), alginate with hydroxypropyl methylcellulose (AK3), and alginate with hydroxypropyl methylcellulose and PLURONIC L61 surfactant (AK3 61). The alginate formulation gave a mean volume size of 11 μm, whereas the addition of methylcellulose to the alginate formulation resulted in microparticles with mean volume size of 10.5 μm. When PLURONIC L61 surfactant was added to the alginate plus methylcellulose formulation, the mean volume size was 3.8 μm. The alginate plus hydroxypropyl methylcellulose formulation resulted in microparticles with mean volume size of 8.7 μm. When PLURONIC L61 surfactant was added to the AK3 formulation, the mean volume size was reduced to 3.9 μm. Poly-1-lysine coating did not result in mean volume size change.

Figure 23:
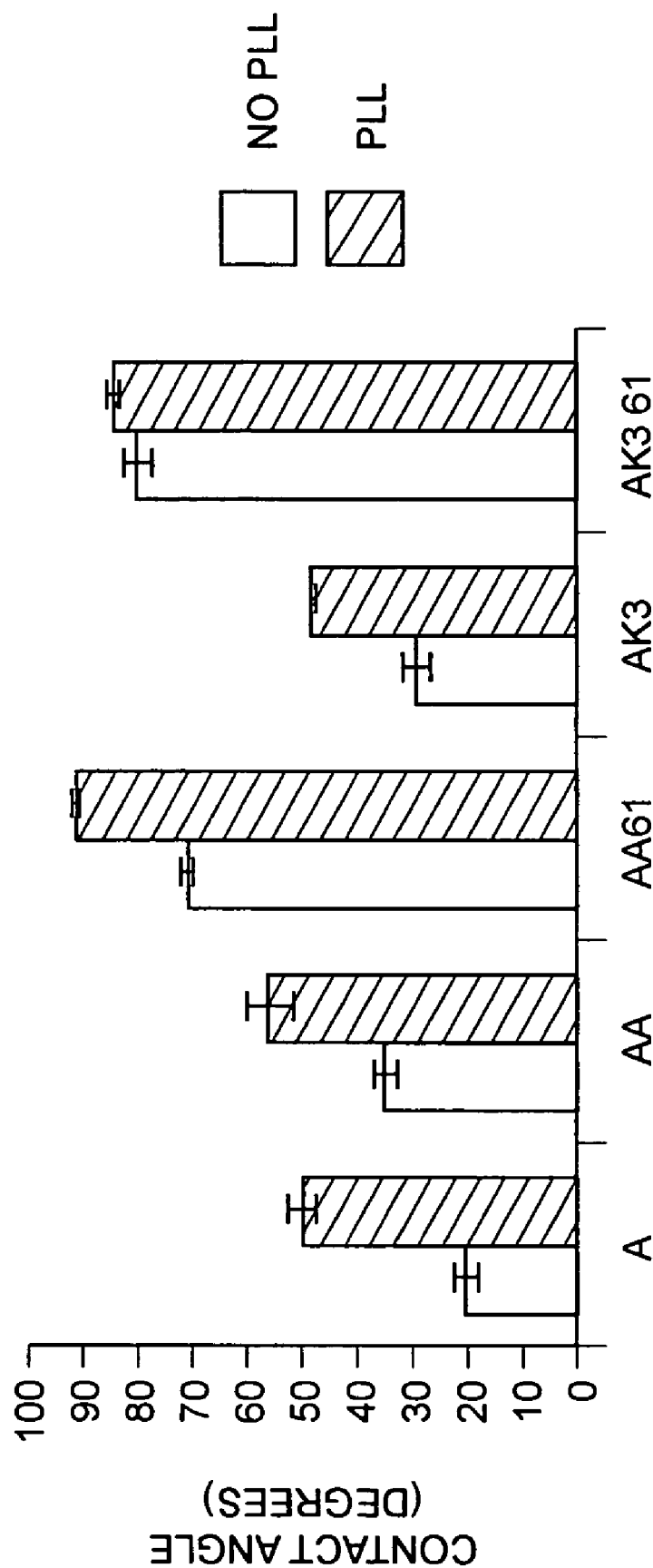

A contact angle goniometer was used to measure the water contact angle on the microparticle-coated glass slides. FIG. 23 shows the contact angles measured for the different formulations. The alginate alone formulation was the most hydrophilic with a contact angle of 20°. When the alginate microparticles were coated with PLL, the contact angle increased to 49.7°. The contact angles on the alginate plus methylcellulose formulation, without and with PLL coating, were 34.8°, and 55.8°, respectively. Incorporation of PLURONIC L61 surfactant into the alginate plus methylcellulose formulation resulted in increasing the contact angle to 71° without PLL coating, and to 91° with PLL coating. When the alginate formulation with hydroxypropyl methylcellulose was used, the contact angles were 29° and 48.3°, without and with PLL coating, respectively. Incorporation of PLURONIC L61 surfactant into the AK3 formulation resulted in increasing the contact angle to 80° without PLL coating, and to 84.8° with PLL coating, respectively.

Figure 24:
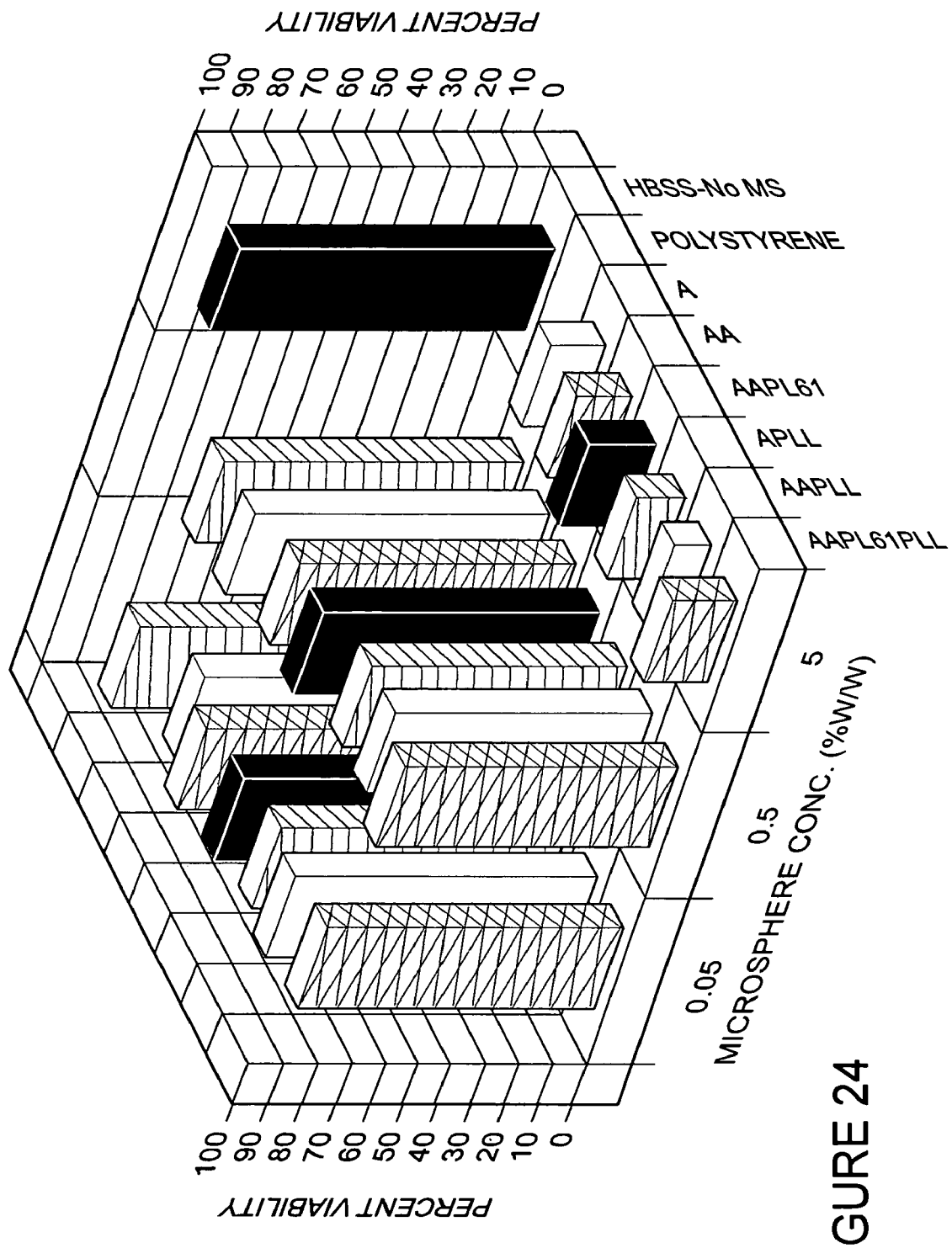

Cytotoxicity of alginate microparticles made from different alginate-based formulations towards bovine PMNs was also examined. The cells were exposed to alginate microparticles for 3 h at 37° C. The cells were then stained with Trypan blue that selectively stains dead PMNs. Both live and dead cells were counted to determine percentage of viable cells. FIG. 24 shows the percentage of total number of cells that survived microparticle exposure. The solid content of the original microparticle suspension was 50%. The microparticle concentrations (% w/w) examined were 0.05%, 0.5%, and 5% in HBSS. HBSS and polystyrene beads were used as controls.

When PMNs were exposed to a 5% (w/v) microparticle suspension in HBSS, 30–39% of the total cells survived for all the formulations except the formulation designated AA61PLL, for which cell viability was 19%. When a 0.5% (w/v) concentration of microparticles was used, cell viability was with in the range of 77–87%, whereas for 0.05% (w/v) microparticle concentration cell viability was between 85% and 96%. There was no statistically significant difference in toxicity to PMNs among the different alginate formulations. There was also no statistically significant difference in toxicity for PMNs between the alginate-based microparticles and polystyrene beads of comparable particle size. There was no statistically significant difference in toxicity to PMNs between PLL coated and un-coated microparticles.

Figure 25:
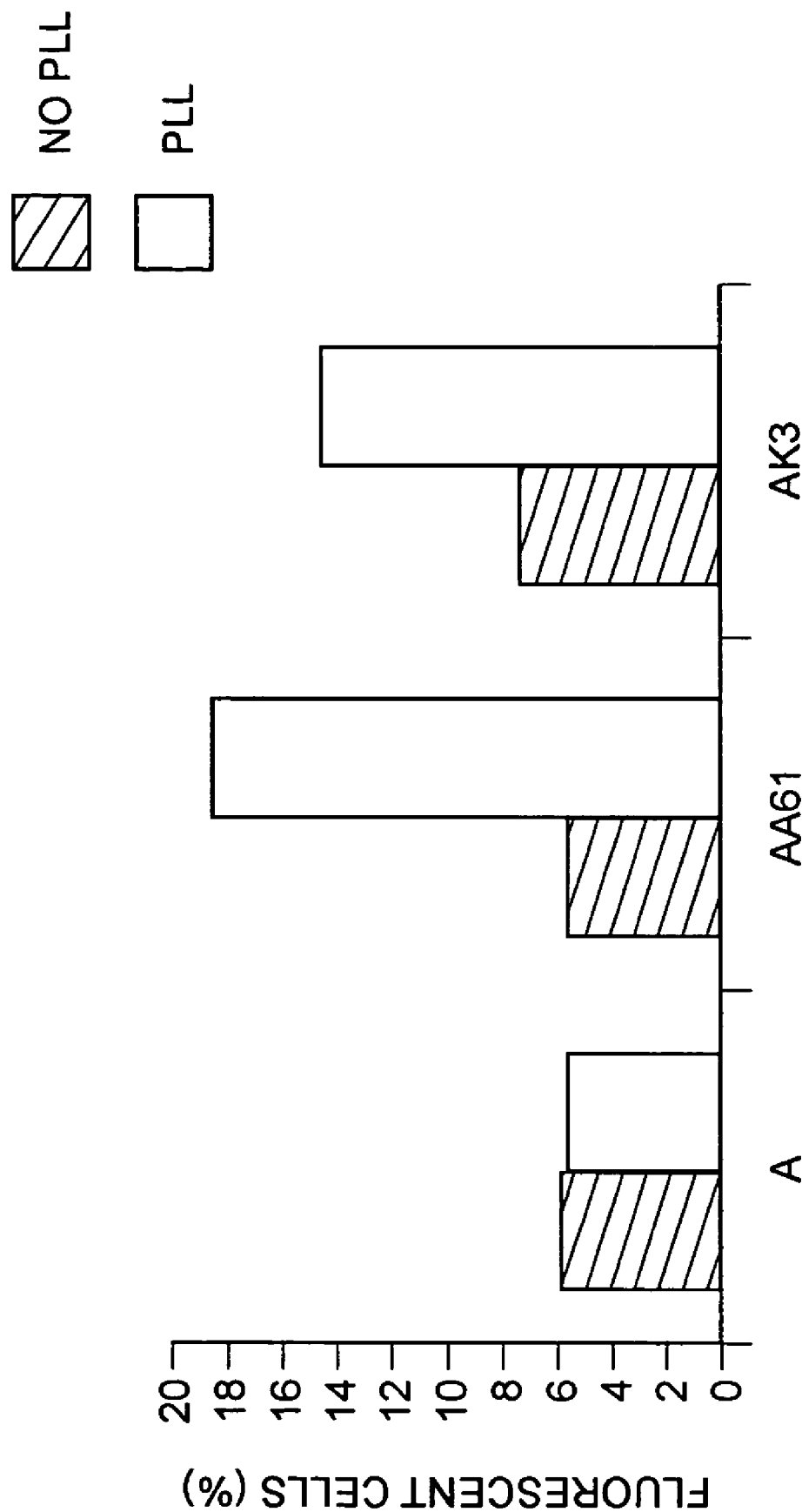

Cellular uptake of alginate microparticles by macrophages was examined using fluorescent labeled microparticles. To be able to discriminate between fluorescent cells and fluorescent FITC-labeled microparticles, cells were stained with propidium iodide (PI) that binds to DNA and fluoresces red in color. Analysis was performed using flow cytometry on PI-positive cells. Percentage of cells whose fluorescence was above a certain cutoff value is reported. The fluorescence cutoff value was chosen so as to exclude cells that had picked up FITC-BSA from solution rather than the microparticles. The same cutoff value was used throughout. FIG. 25 shows the percentage of fluorescent cells for various microparticle preparations. The percent fluorescent cells when macrophages were exposed to alginate (A) microparticles, without and with PLL coating, was 6.0% and 5.7%, respectively. Exposing the cells to alginate microparticles made with methylcellulose plus PLURONIC L61 surfactant (AA61), without and with PLL coating, resulted in fluorescent cells of 5.5% and 18.5%, respectively. Fluorescence obtained when cells were exposed to alginate plus hydroxypropyl methylcellulose (AK3), without and with PLL coating, was 7.4% and 14.7%, respectively.

Alginate microparticles with and without poly-lysine coating showed similar uptake by the mouse macrophage cell line, despite a two-fold difference in hydrophobicity between the two. An alginate formulation that included methylcellulose and PLURONIC L61 (AA61) without and with PLL resulted in microparticles with a mean volume size of about 3.8 µm. This size is roughly 3 times smaller than microparticles obtained from the same process alginate alone and alginate with methylcellulose formulations. Also, the hydrophobicity of the AA61 formulation as measured by contact angle goniometer was 3 times higher than a formulation with alginate alone. Despite these differences in size and hydrophobicity, AA61 microparticles were not taken up any better than alginate alone and alginate with cellulose derivatives. Coating alginate microparticles (made without surfactants) with PLL did not improve uptake by mouse macrophages. However, coating AA61 microparticles with PLL improved cellular uptake by 3 fold. Also, PLL coated alginate microparticles made with hydroxypropyl methylcellulose were taken up better compared to microparticles without PLL. This pattern of cellular uptake that does not follow either microparticle size or hydrophobicity individually can result from the combined effects of size, hydrophobicity and cellular interaction with the microparticle surface.

All the formulations examined, while showing a concentration dependent toxicity to bovine PMNs, failed to show a formulation dependent toxicity. The most concentrated microparticle suspension resulted in the most cellular death. However, both 10- and 100-times dilutions of the same microparticle suspension did not result in any significant toxicity when compared to the negative control. This indicates that formulation components used in making alginate-based microparticles are safe.

The foregoing description is given for clearness of understanding only, and no unnecessary limitations should be understood therefrom, as modifications within the scope of the invention may be apparent to those having ordinary skill in the art.

What is claimed is:

1. A method of vaccinating a vertebrate species, comprising administering to a vertebrate species a vaccine comprising a composition prepared by:
   (A) forming a water-in-oil emulsion comprising
      (a) water,
      (b) an alginate,
      (c) an oil,
      (d) an antigen, and
      (e) a surfactant composition comprising at least one of
         (i) a cellulose ether and at least one nonionic surfactant and
         (ii) a poly(ethylene oxide)-poly(propylene oxide)-poly(ethylene oxide) triblock copolymer surfactant and at least one nonionic surfactant;
   (B) crosslinking the alginate in the emulsion of step (A) with at least two different cations selected from the group consisting of aluminum, barium, calcium, manganese, strontium, and zinc, to form antigen-containing crosslinked alginate microparticles; and
   (C) harvesting the microparticles of step (B).

2. The method of claim 1 wherein the microparticles are less than about 10 µm in diameter.

3. The method of claim 1 wherein the cellulose ether is selected from the group consisting of ethylcellulose, methylcellulose, hydroxymethylcellulose, hydroxypropylcellulose, hydroxypropyl methylcellulose, and mixtures thereof.

4. The method of claim 1 wherein at least one of said nonionic surfactants of steps (A)(e)(i) and (ii) is selected from the group consisting of polyoxyethylene surfactants, anhydrosorbitol ester surfactants, ethoxylated anhydrosorbitol ester surfactants, and mixtures thereof.

5. The method of claim 4 wherein said polyoxyethylene surfactant is an alcohol ethoxylate.

6. The method of claim 5 wherein said alcohol ethoxylate is polyoxyethylene (2) olyl ether.

7. The method of claim 4 wherein said nonionic surfactant is an anhydrosorbitol ester.

8. The method of claim 7 wherein said anhydrosorbitol ester is sorbitan trioleate.

9. The method of claim 4 wherein said nonionic surfactant is an ethoxylated anhydrosorbitol ester.

10. The method of claim 9 wherein said ethoxylated anhydrosorbitol ester is polyoxyethylene sorbitan trioleate.

11. The method of claim 1 wherein said poly(ethylene oxide)-poly(propylene oxide)-poly(ethylene oxide) triblock copolymer has from about 15 to about 70 propylene oxide residues.

12. The method of claim 11 wherein said poly(ethylene oxide)-poly(propylene oxide)-poly(ethylene oxide) triblock copolymer has about 30 propylene oxide residues.

13. The method of claim 11 wherein said poly(ethylene oxide)-poly(propylene oxide)-poly(ethylene oxide) triblock copolymer has the formula $(EO)_3(PO)_{30}(EO)_3$.

14. The method of claim 1 wherein the antigen is selected from the group consisting of live virus, live bacteria, killed virus, killed bacteria, subunit antigens of infectious agents, and mixtures thereof.

15. The method of claim 1 wherein the cations comprise calcium and zinc.

16. The method of claim 1 wherein said emulsion comprises sources of said cations selected from the group consisting of $AlSO_4$, $BaCl_2$, $CaCl_2$, $MnCl_2$, $ZnCl_2$, calcium acetate, zinc acetate, strontium nitrate, and mixtures thereof.

17. The method of claim 16 wherein the sources of cations comprise $CaCl_2$ and $ZnCl_2$.

18. The method of claim 16 wherein the sources of cations comprise calcium acetate and zinc acetate.

19. The method of claim 1 wherein the emulsion of step (A) further comprises poly(propylene glycol).

20. The method of claim 1 wherein the emulsion of step (A) comprises said cellulose ether and at least two nonionic surfactants.

21. The method of claim 1 further comprising, prior to step (A), the step of adding at least one nonionic surfactant to the oil.

22. The method of claim 1 comprising the step of coating the microparticles harvested in step (C) with a polymer.

23. The method of claim 22 wherein the polymer is a poly-cation.

24. The method of claim 23 wherein the poly-cation is selected from the group consisting of poly-1-lysine, poly-histidine, polyarginine, polyethyleneimine, and mixtures thereof.

25. The method of claim 24 wherein the poly-cation is poly-1-lysine.

26. The method of claim 1 comprising the step of coating the microparticles harvested in step (C) with a mucosal adjuvant/adhesant.

27. The method of claim 26 wherein the mucosal adjuvant/adhesant is selected from the group consisting of lectins, cholera toxin, B subunit toxin of cholera toxin, recombinant derived subunits of B subunit toxin of cholera toxin, pertussis toxin, heat labile toxin of *E. coli*, exotoxin A of *P. aeruginosa*, and mixtures thereof.

28. The method of claim 1 wherein step (B) comprises adding the cations to the emulsion of step (A) in dropwise fashion, while stirring the emulsion at a speed of at least about 1,000 RPM.

29. The method of claim 1 wherein at least one of said nonionic surfactant of steps (A)(e)(i) and (ii) and said poly(ethylene oxide)-poly(propylene oxide)-poly(ethylene oxide) triblock copolymer has a hydrophile/lipophile balance from about 1 to about 15.

30. The method of claim 1 wherein said surfactant composition has a hydrophile/lipophile balance of about 8.3.

31. The method of claim 1 wherein the emulsion comprises said poly(ethylene oxide)-poly(propylene oxide)-poly(ethylene oxide) triblock copolymer and said nonionic surfactant is an ethoxylated anhydrosorbitol ester surfactant.

32. The method of claim 31 wherein said ethoxylated anhydrosorbitol ester surfactant comprises polyoxyethylene sorbitan trioleate.

33. The method of claim 32 wherein said poly(ethylene oxide)-poly(propylene oxide)-poly(ethylene oxide) triblock copolymer has the formula $(EO)_3(PO)_{30}(EO)_3$.

34. The method of claim 33 wherein the emulsion further comprises said cellulose ether.

35. The method of claim 1, wherein said administering is performed orally.

36. A method of vaccinating a vertebrate species, comprising administering to a vertebrate species a composition comprising a multi-cation cross-linked alginate comprising an antigen, a nonionic surfactant, and one or both of a cellulose ether and a poly(ethylene oxide)-poly(propylene oxide)-poly(ethylene oxide) triblock copolymer surfactant,
the cations of said multi-cation crosslinked alginate selected from at least two different members of the group consisting of aluminum, barium, calcium, manganese, strontium, and zinc.

37. The method of claim 36 wherein the alginate is in the form of microparticles which are less than about 10 μm in diameter.

38. The method of claim 36 wherein the cellulose ether is selected from the group consisting of ethylcellulose, methylcellulose, hydroxymethylcellulose, hydroxypropylcellulose, hydroxypropyl methylcellulose, and mixtures thereof.

39. The method of claim 36 wherein said nonionic surfactant is selected from the group consisting of polyoxyethylene surfactants, anhydrosorbitol ester surfactants, ethoxylated anhydrosorbitol ester surfactants, and mixtures thereof.

40. The method of claim 39 wherein said polyoxyethylene surfactant is an alcohol ethoxylate.

41. The method of claim 40 wherein said alcohol ethoxylate is polyoxyethylene (2) olyl ether.

42. The method of claim 39 wherein said nonionic surfactant is an anhydrosorbitol ester.

43. The method of claim 42 wherein said anhydrosorbitol ester is sorbitan trioleate.

44. The method of claim 39 wherein said nonionic surfactant is an ethoxylated anhydrosorbitol ester.

45. The method of claim 44 wherein said ethoxylated anhydrosorbitol ester is polyoxyethylene sorbitan trioleate.

46. The method of claim 36 wherein said poly(ethylene oxide)-poly(propylene oxide)-poly(ethylene oxide) triblock copolymer has from about 15 to about 70 propylene oxide residues.

47. The method of claim 46 wherein said poly(ethylene oxide)-poly(propylene oxide)-poly(ethylene oxide) triblock copolymer has about 30 propylene oxide residues.

48. The method of claim 46 wherein said poly(ethylene oxide)-poly(propylene oxide)-poly(ethylene oxide) triblock copolymer has the formula $(EO)_3(PO)_{30}(EO)_3$.

49. The method of claim 36 wherein the antigen is selected from the group consisting of live virus, live bacteria, killed virus, killed bacteria, subunit antigens of infectious agents, and mixtures thereof.

50. The method of claim 36 wherein the cations comprise calcium and zinc.

51. The method of claim 36 wherein the alginate further comprises poly(propylene glycol).

52. The method of claim 36 wherein the alginate comprises said cellulose ether and at least two nonionic surfactants.

53. The method of claim 36 comprising the step of coating the alginate with a polymer prior to said administering.

54. The method of claim 53 wherein the polymer is a poly-cation.

55. The method of claim 54 wherein the poly-cation is selected from the group consisting of poly-1-lysine, poly-histidine, polyarginine, polyethyleneimine, and mixtures thereof.

56. The method of claim 55 wherein the poly-cation is poly-1-lysine.

57. The method of claim 36 comprising the step of coating the alginate with a mucosal adjuvant/adhesant prior to said administering.

58. The method of claim 57 wherein the mucosal adjuvant/adhesant is selected from the group consisting of lectins, cholera toxin, B subunit toxin of cholera toxin, recombinant derived subunits of B subunit toxin of cholera toxin, pertussis toxin, heat labile toxin of E. coli, exotoxin A of P. aeruginosa, and mixtures thereof.

59. The method of claim 36 wherein at least one of said nonionic surfactant and said poly(ethylene oxide)-poly(propylene oxide)-poly(ethylene oxide) triblock copolymer has a hydrophile/lipophile balance from about 1 to about 15.

60. The method of claim 36 wherein said surfactant composition has a hydrophile/lipophile balance of about 8.3.

61. The method of claim 36 wherein the alginate comprises said poly(ethylene oxide)-poly(propylene oxide)-poly(ethylene oxide) triblock copolymer and said nonionic surfactant is an ethoxylated anhydrosorbitol ester surfactant.

62. The method of claim 61 wherein said ethoxylated anhydrosorbitol ester surfactant comprises polyoxyethylene sorbitan trioleate.

63. The method of claim 62 wherein said poly(ethylene oxide)-poly(propylene oxide)-poly(ethylene oxide) triblock copolymer has the formula $(EO)_3(PO)_{30}(EO)_3$.

64. The method of claim 63 wherein the alginate further comprises said cellulose ether.

65. The method of claim 36 wherein said administering is performed orally.

* * * * *